United States Patent [19]
Jarrett et al.

[11] Patent Number: 5,324,307
[45] Date of Patent: Jun. 28, 1994

[54] POLYMERIC SURGICAL STAPLE

[75] Inventors: Peter K. Jarrett, Southbury, Conn.; Donald J. Casey, Mars, Pa.; Louis Rosati, Norwalk; James W. Dwyer, Brookfield, both of Conn.

[73] Assignee: American Cyanamid Company, Wayne, N.J.

[21] Appl. No.: 799,521

[22] Filed: Nov. 27, 1991

Related U.S. Application Data

[63] Continuation-in-part of Ser. No. 548,802, Jul. 6, 1990, Pat. No. 5,080,665.

[51] Int. Cl.$^5$ .............................. A61B 17/00
[52] U.S. Cl. .................. 606/219; 525/415; 528/354; 528/357
[58] Field of Search ........ 606/219; 528/370, 354–357; 524/381; 523/354, 359, 361, 105, 113; 428/395; 227/110; 525/415

[56] References Cited

U.S. PATENT DOCUMENTS

| | | | |
|---|---|---|---|
| 4,045,418 | 8/1977 | Sinclair . | |
| 4,057,537 | 11/1977 | Sinclair . | |
| 4,262,836 | 4/1981 | Hirose | 227/110 |
| 4,300,565 | 11/1981 | Rosensaft et al. | 528/354 |
| 4,523,591 | 6/1985 | Kaplan et al. | 128/334 R |
| 4,595,713 | 6/1986 | St. John | 523/105 |
| 4,605,730 | 8/1986 | Shalaby et al. | 528/357 |
| 4,671,280 | 6/1987 | Dorband et al. | 128/334 C |
| 4,700,704 | 10/1987 | Jamiolkowski et al. | |
| 4,705,820 | 11/1987 | Wang et al. | 524/381 |
| 4,719,917 | 1/1988 | Barrows et al. | 128/334 R |
| 4,744,365 | 5/1988 | Kaplan et al. | 128/335.5 |
| 4,788,979 | 12/1988 | Jarrett | 528/354 |
| 4,839,130 | 6/1989 | Kaplan et al. | 264/235 |
| 4,844,854 | 7/1989 | Kaplan et al. | 264/235 |
| 4,916,193 | 4/1990 | Tang et al. | 525/413 |
| 4,920,203 | 4/1990 | Tang et al. | 525/409 |
| 4,976,909 | 12/1990 | Dorband et al. | 264/235 |
| 4,994,073 | 2/1991 | Green | 606/220 |
| 5,133,739 | 7/1992 | Bezwada et al. | 606/230 |

Primary Examiner—Stephen C. Pellegrino
Assistant Examiner—Gary Jackson
Attorney, Agent, or Firm—Charles F. Costello, Jr.

[57] ABSTRACT

A one piece surgical repair device consists essentially of a polymeric wire. The polymeric wire is comprised of an oriented, semicrystalline polymer. The surgical repair device can be a staple and is capable of permanent flexural deformation at ambient temperature.

46 Claims, 4 Drawing Sheets

POLYMERIC SURGICAL STAPLE

This is continuation in part application of U.S. Ser. No. 07/548,802 filed Jul. 6, 1990, now U.S. Pat. No. 5,080,665.

BACKGROUND OF THE INVENTION

This invention relates to surgical staples formed from an extruded "polymeric wire." . The term "wire," as used in describing this invention, includes both polymeric and metallic monofilaments. It has been found that wire (or monofilament fiber) extruded from polymer that is normally rigid at in vivo conditions can be used to form a surgical staple. The formation of a staple using the polymeric wire is accomplished using standard methods employed in the manufacture of metallic staples used in the surgical staple industry. Normally rigid polymers, when oriented by extrusion into polymeric wire according to this invention, have enhanced ductility in flexure. The terms "ductile" and "ductility" as used in describing this invention denote the property of permanent deformability, or plasticity, which may result from processes such as crazing or yielding. Specifically, ductile polymeric wires, when bent, will retain a large portion of the bend angle permanently (note that it is not required that the polymeric wires of this invention be ductile in tension along the fiber axis, only in bending or flexure) and the application of work is required to unbend the bent wire. This property can be used to form surgical staples simply by bending the polymeric wire as is done for metallic staples. This type of staple has great advantages over the types of staples in use today.

The current commercially available plastic staples are two-piece, injection molded devices. These staples are relatively large due to the need for the incorporation of an interlocking mechanism for joining the two staple pieces. The staples of the present invention have no requirement for an interlocking mechanism because the final form of the staple is accomplished simply by bending the polymeric wire, exactly as is done for metallic wires. The polymeric wire, not being as stiff as metal, requires a somewhat larger diameter to provide adequate holding power, but the final size is much more acceptable to the surgeon than the currently available plastic surgical staples.

The polymeric wire also has advantages over metallic wire. Metallic staples are known to be highly radiopaque, causing difficulties in reading X-ray images (both conventional and CT (Computed Tomography) scanning images) as well as MRI (Magnetic Resonance Imaging) images due to what is known as the "starburst effect," a result of the high contrast of the metal to the tissue. These small areas of high contrast can cause difficulties in interpreting these images for subtle diagnostic purposes. Most polymers are known to be much more radio-transparent than metals. The reduced contrast between polymeric staples and tissue using these radio-imaging techniques eliminates the starburst effect. An additional advantage of polymeric staples over metal is that the polymeric staples can be formed from bioabsorbable polymers; thus, eliminating the risk of long term foreign body reactions of the tissue or staple migration that may be encountered with metal staples.

The patent and medical literature dealing with metallic staples and their uses in surgery is quite extensive. A review of surgical procedures involving internal staples and stapling devices can be found in "Stapling in Surgery", F. M. Steichen and M. M. Ravitch, Year Book Medical Publishers, Inc., Chicago, 1984, which is incorporated herein by reference. Because of the obvious differences between metallic and polymeric staples, a detailed review of metallic staples is not necessary to illustrate the uniqueness of the present invention.

With regard to polymeric staples, a number of patents and journal articles have appeared which describe the advantages of polymeric materials for staple applications. The majority of these publications describe a preference for absorbable polymers. The following U.S. patents are background to the present invention described in this application: U.S. Pat. Nos. 4,994,073, 4,976,909, 4,889,119, 4,844,854, 4,839,130, 4,805,617, 4,744,365, 4,741,337, 4,719,917, 4,671,280, 4,646,741, 4,612,923, 4,610,250, 4,602,634, 4,589,416, 4,573,469, 4,532,926, 4,523,591, 4,513,746, 4,428,376, 4,402,445, 4,317,451, 4,272,002, 4,060,089, 4,006,747. All of these patents are incorporated herein by reference.

Almost all of the above patents describe various polymeric materials for use in two-part, molded (not extruded) snap-together staples of various designs. These staples are not made from extruded, oriented polymeric wire and are not bent to form the final, implanted, staple shape. Two patents, U.S. Pat. No. 4,976,909 and U.S. Pat. No. 4,671,280, describe a two-piece staple where one of the components is formed from an extruded, "oriented crystalline polymeric material". The final, implanted, staple form is achieved by mating the extruded portion with a molded portion, not by bending the oriented component. Two of the above cited patents, U.S. Pat. No. 4,428,376 and U.S. Pat. No. 4,317,451, describe one-piece staples made of absorbable or non-absorbable polymers. These patents describe a mechanical looking-hinge mechanism to hold the staple legs in their final configuration. Application of the devices described in these patents to tissue is accomplished by bending at the hinge point until the locking mechanism engages. The devices described are not formed from extruded polymeric wire and are not formed or applied by bending an extruded polymeric wire. Another patent, U.S. Pat. No. 4,994,075, describes a one-piece molded device that uses two barbed prongs to hold the tissue. This device is not formed from extruded polymeric wire and it is not formed or applied to tissue by bending.

The disclosure in the patent application, U.S. Ser. No. 07/548,802 filed on Jul. 6, 1990, now U.S. Pat. No. 5,080,665 by P. K. Jarrett, D. J. Casey and S. L. Peake, entitled "Deformable, Absorbable Surgical Device" and assigned to American Cyanamid Co., Stamford, Conn. 06904-0060 is incorporated herein by reference. This patent application describes, e.g., in claims 1 and 10, a clip or staple manufactured from a copolymer or blend.

SUMMARY AND DETAILED DESCRIPTION OF THE INVENTION

The invention is more fully described by the following embodiments:

1. An article of manufacture comprising a one piece surgical repair device consisting essentially of a polymeric wire manufactured from an oriented, semicrystalline polymer, wherein the one piece surgical repair device is capable of permanent flexural deformation at ambient temperature.

2. The article of embodiment 1 wherein the polymeric wire has a diameter of about 0.005 to 0.050 inches.

3. The article of embodiment 2 wherein the diameter is about 0.010 to 0.025 inches.

4. The article of embodiment 1 or 2 or 3 wherein the polymeric wire has a Young's modulus of greater than about 600,000 psi.

5. The article of embodiment 4 wherein the Young's modulus is greater than about 800,000 psi.

6. The article of embodiment 6 wherein the oriented polymer is from about 20 to 70 percent crystalline.

7. The article of embodiment 6 wherein said oriented polymer is up to about 60 percent crystalline.

8. The article of embodiment 1 wherein the oriented, semicrystalline polymer has at least one continuous phase.

9. The article of embodiment 8 wherein said oriented, semicrystalline polymer is a homopolymer of polylactic acid.

10. The article of embodiment 8 wherein said oriented, semicrystalline polymer is a homopolymer of polyglycolic acid.

11. The article of embodiment 8 wherein said oriented, semicrystalline polymer is a block copolymer.

12. The article of embodiment 8 wherein said oriented, semicrystalline polymer is a multi-phase polymer derived from lactide and glycolide. For this embodiment and embodiments 30 and 68 below, the U.S. Pat. Nos. 4,744,365, 4,839,130, and 4,844,854 (also cited above) disclose how to make and use a multi-phase polymer derived from lactide and glycolide. For example, the '130 patent describes a process for making an annealed staple, and the '365 and '854 patents respectively describe an injection molded staple and a process for making it. These patents were issued in 1988–1989 and are assigned to United States Surgical Corp., Norwalk, Conn.

13. The article of embodiment 11 wherein the block copolymer comprises lactic acid ester linkages.

14. The article of embodiment 13 wherein said block copolymer comprises linkages prepared from monomers selected from the group consisting of ε-caprolactone and 1,3-dioxan-2-one.

15. The article of embodiment 14 wherein the lactic acid ester linkages comprise about 95 mole percent of said block copolymer.

16. The article of embodiment 15 wherein the remaining linkages are prepared from 1,3-dioxan-2-one.

17. The article of embodiment 15 wherein the remaining linkages are prepared from ε-caprolactone.

18. The article in any one of embodiment 8 to 17 wherein at least one of the one or more continuous phases have an in vivo glass transition temperature of more than about 37° C.

19. The article in any one of embodiments 11 to 17 wherein at least one of the continuous phases has an in vivo glass transition temperature of more than about 37° C. and comprises more than about 50 mole percent of the copolymer.

20. The article in any one of embodiments 1 to 3 or 6 to 17 wherein the one piece surgical repair device is a staple.

21. The article in any one of embodiments 1 to 3 or 6 to 17 wherein the one piece surgical repair device is a cerclage wire or Kirschner wire. For this embodiment and embodiments 33, 56 and 64 (cerclage wire), and 57 and 65 (Kirschner wire) below, metal cerclage and Kirschner wires are disclosed in the prior art, e.g. "Posterior Cervical Fusions Using Cerclage Wires, . . . ", R. Whitehall, et al., Spine vol. 12 pages 12–22, 1987 and "Compression-Arthrodesis of Finger Joints Using Kirschner Wires and Cerclage", J. Hogh et al., Hand vol. 14 pages 149–52, 1982. Both of these articles are incorporated herein by reference.

22. An article of manufacture comprising a one piece surgical staple consisting essentially of a polymeric wire comprised of an oriented, semicrystalline block copolymer having at least one continuous phase, and comprising more than about 50 mole percent of lactic acid ester linkages and the remaining linkages are prepared from ε-caprolactone, wherein the one piece surgical staple is capable of permanent flexural deformation at ambient temperature.

23. An article of manufacture comprising a one piece, sterile surgical repair device manufactured from a polymeric wire comprising an extrusile, biocompatible polymer having one or more continuous phases, at least one of the continuous phases having an in vivo glass transition temperature of more than about 37° C., wherein the one piece, sterile surgical repair device is capable of permanent flexural deformation at ambient temperature.

24. The article of embodiment 23 wherein the polymeric wire has a diameter of about 0.005 to 0.50 inches.

25. The article of embodiment 24 wherein the diameter is about 0.010 to 0.025 inches.

26. The article of embodiment 23 or 24 or 25 wherein the polymeric wire has a Young's modulus of greater than about 600,000 psi.

27. The article of embodiment 26 wherein the Young's modulus is greater than about 800,000 psi.

28. The article of embodiment 23 wherein the extrusile, biocompatible polymer is a copolymer.

29. The article of embodiment 28 wherein the copolymer is a block copolymer.

30. The article of embodiment 23 wherein the extrusile, biocompatible polymer is a multi-phase polymer derived from two different monomers.

31. The article of embodiment 28 or 29 or 30 wherein at least one of the one or more continuous phases has an in vivo glass transition temperature of more than about 37° C. and comprises more than about 50 mole percent of the copolymer.

32. The article in any one of the embodiments 23 to 25 or 28 to 30 wherein the one piece surgical repair device is a staple and the polymeric wire has a Young's modulus of greater than about 600,000 psi.

33. The article in any one of embodiments 23 to 25 or 28 to 30 wherein the one piece surgical repair device is a cerclage wire.

34. A one piece, sterile surgical staple useful in mammalian tissue, the staple comprising an extruded polymeric wire consisting essentially of an oriented, semicrystalline bioabsorbable polymer, or blend of two or more polymers wherein at least one polymer is a semicrystalline polymer, the oriented, semicrystalline bioabsorbable polymer or blend comprising a continuous phase having a glass transition temperature of greater than the in-vivo temperature of the mammalian tissue, wherein said staple is capable of permanent deformation in body fluids.

35. An article of manufacture comprising an irradiation sterilized, surgical staple manufactured from an extruded and drawn polymeric wire having a diameter of about 0.005 to 0.050 inches, the polymeric wire comprising a bioabsorbable polymer having one or more continuous phases, at least one of the continuous phases having an in vivo glass transition temperature of more than about 37° C., wherein the irradiation sterilized, surgical staple is capable of permanent flexural deformation, has a Young's modulus of greater than about 800,000 psi, and maintains at least about 50 percent of its initial opening strength after 21 days in vivo.

36. The article of embodiment 35 wherein said irradiation sterilized, surgical staple is one piece.

37. The article of embodiment 35 wherein the extruded and drawn polymeric wire has a diameter of about 0.010 to 0.025 inches.

38. The article of embodiment 36 wherein the bioabsorbable polymer is a homopolymer of polylactic acid.

39. The article of embodiment 36 wherein the bioabsorbable polymer is a homopolymer of polyglycolic acid.

40. The article of embodiment 35 wherein the bioabsorbable polymer is a copolymer.

41. The article of embodiment 40 wherein the copolymer comprises more than about 50 mole percent of glycolic acid ester linkages.

42. The article of embodiment 41 wherein said irradiation sterilized, surgical staple maintains about 100 percent after 7 days and greater than about 70 percent after 21 days in vivo of its initial opening strength.

43. The article of embodiment 40 wherein the copolymer comprises lactic acid ester linkages.

44. The article of embodiment 43 wherein the block copolymer comprises linkages prepared from monomers selected from the group consisting of ε-caprolactone and 1,3-dioxan-2-one.

45. The article of embodiment 43 wherein the copolymer is a block copolymer and comprises more than about 50 mole percent of lactic acid ester linkages.

46. The article of embodiment 45 wherein the remaining linkages are prepared from 1,3-dioxan-2-one.

47. An article of manufacture comprising an irradiation sterilized, surgical staple consisting essentially of an extruded and drawn polymeric wire having a diameter of about 0.005 to 0.050 inches, the polymeric wire comprising a bioabsorbable block copolymer having at least about 80 mole percent of lactic acid ester linkages and the remaining linkages are prepared from ε-caprolactone, and comprising one or more continuous phases, at least one of the continuous phases having an in vivo glass transition temperature of more than about 37° C., wherein the irradiation sterilized, surgical staple is capable of permanent flexural deformation, has a Young's modulus of greater than about 800,000 psi, and maintains at least about 50 percent of its initial opening strength after 21 days in vivo.

48. The article of embodiment 46 or 47 wherein the lactic acid ester linkages comprise about 95 mole percent of the block copolymer.

49. The article as in any one of embodiments 43 to 47 wherein said irradiation sterilized, surgical staple maintains greater than about 110 percent of its initial opening strength from about 7 to 21 days in vivo.

50. A process for manufacturing a one piece surgical repair device capable of permanent flexural deformation at ambient temperature, the process comprising:
    extruding a semicrystalline polymer through a single jet to orient the semicrystalline polymer and form a polymeric wire;
    quenching the polymeric wire at about 25° C.;
    drawing said polymeric wire in at least one stage at a draw ratio of greater than 1× to less than about 12×;
    forming at least one curve in said polymeric wire by bending it over a fixture having at least one curved surface; and
    cutting at least one end of said polymeric wire to form the one piece surgical repair device.

51. The process of embodiment 50 wherein the single jet in the extruding step has a diameter of about 0.05 to 0.15 inches.

52. The process of embodiment 51 having two stages in the drawing step, the draw ratio of the first stage being greater than 4× to less than 7× and the draw ratio of the second stage being less than 2×.

53. The process of embodiment 52 wherein the fixture in the bending step has two curved surfaces.

54. The process of embodiment 53 wherein the cutting step comprises shearing both ends of said polymeric wire at an oblique angle to its axial direction.

55. The process of embodiment 54 wherein said one piece surgical repair device is a staple.

56. The process of embodiment 52 wherein said one piece surgical repair device is a cerclage wire.

57. The process of embodiment 52 wherein said one piece surgical repair device is a Kirschner wire.

58. A process for sterilizing a one piece bioabsorbable surgical repair device capable of permanent flexural deformation at ambient temperature, the one piece bioabsorbable surgical repair device comprising a polymeric wire having lactic acid ester linkages, the process comprising:
    irradiating said one piece bioabsorbable surgical repair device.

59. The process of embodiment 58 wherein the irradiating step comprises gamma irradiating.

60. The process of embodiment 59 wherein said irradiating step comprises a dose of greater than about 2 Mrads.

61. The process of embodiment 60 wherein said irradiating step comprises a dose of up to about 7 Mrads.

62. The process of embodiment 59 wherein said one piece surgical staple in said irradiating step is exposed to Cobalt 60 radiation.

63. The process of embodiment 59 wherein said one piece surgical repair device is a staple.

64. The process of embodiment 59 wherein said one piece surgical repair device is a cerclage wire.

65. The process of embodiment 59 wherein said one piece surgical repair device is a Kirschner wire.

66. The process of any one of embodiments 58 to 65 wherein the polymeric wire is comprised of an oriented, semicrystalline polymer.

67. The article of embodiment 66 wherein said oriented, semicrystalline polymer is a block copolymer.

68. The article of embodiment 66 wherein said oriented, semicrystalline polymer is a multi-phase polymer derived from lactide and glycolide.

69. The article of embodiment 67 wherein said block copolymer comprises linkages prepared from monomers selected from the group consisting of ε-caprolactone and 1,3-dioxan-2-one.

70. The process of embodiment 69 wherein the lactic acid ester linkages comprise at least about 80 mole percent of said block copolymer.

71. The article of embodiment 70 wherein the remaining linkages are prepared from 1,3-dioxan-2-one.

72. The article of embodiment 70 wherein the remaining linkages are prepared from ε-caprolactone.

DETAILED DESCRIPTION

Figure 1:
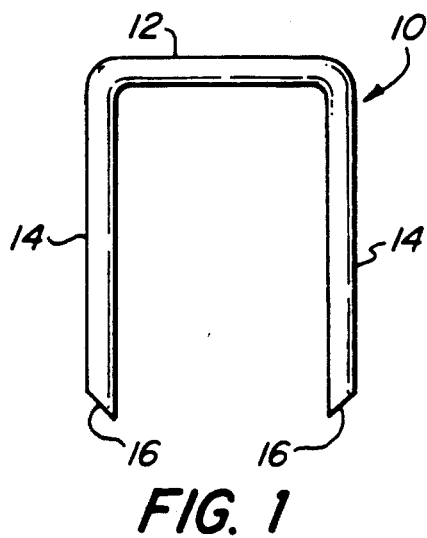
FIGS. 1 and 2 are side views of a preformed and deformed staple of this invention.

Surgical staples in use today appear in a number of forms, as required for the variety of types of procedures for which staples are used. A number of materials are used, but by a large margin the most commonly used material is stainless steel. One form currently used with metallic staples is what is known as a "B" shaped (see "Stapling in Surgery", F. M. Steichen and M. M. Ravitch, Year Book Medical Publishers, Inc., Chicago, 1984, page 83: "As in almost all the stapling instruments, beginning with Hultl's, the staples for suturing parenchymal organs begin in a squared-off U and close in a B, which is non-strangulating, nonnecrosing, and permits vessels to pass through the staple loops.") staple, typically used in internal procedures such as organ resections or bowel anastomoses. Prior to application of the staple to the tissue, the B staple "preform" resembles a squared-off version of the letter U—very similar to the familiar paper staple. During the application of the B staple the "legs" of the staple are bent after passing through the tissue to form a shape resembling the letter B. The B shape is desirable as it provides a secure joining of tissue and stops blood flow from larger blood vessels, while allowing blood flow through smaller vessels (e.g. 1 mm in diameter or less) to continue; thus, preventing necrosis of the tissue to which the staple is attached. Another shape used with metals is the "box" staple, typically used for procedures such as fascia or skin closure. During application of this staple, the "backspan" of the staple preform (a shallow U shape) is bent at two points to form the final square or rectangular form. Other shapes are used as well, and all of the metallic forms (to our knowledge) require bending of the staple during application to the tissue to achieve the final staple shape.

It has been found that it is possible to produce staples for surgical use from polymeric wire. The requirements for a suitable polymer are that it be extrudable to form a monofilament of the required diameter and that it be permanently deformable (bendable) at room or body conditions. We have found that polymeric wire that is normally rigid at body conditions of temperature and moisture perform well. The best results have been obtained with materials that have glass transition temperatures in excess of body temperature. Polymeric wire that is more flexible will not hold a permanent bend as well as rigid polymeric wire staples.

It has also been found that many bioabsorbable polymers can be successfully made into staples. Polymers such as polyglycolide and polylactide can be extruded to form monofilament polymeric wire, provided they have adequate melt viscosity properties. These polymeric wires can then be bent and formed into staples.

It has also been found that bioabsorbable copolymers can be successfully made into staples. Such copolymers may exhibit more than one solid phase, with at least one of the phases being continuous, i.e. the phase extends throughout the continuum of the staple without interruption or break. In this case it is desirable that the predominant continuous phase of the copolymer (if multiple phases are present) have a glass transition temperature above use temperature. The copolymer can have any type of molecular architecture (e.g. statistical (random), segmented, block, graft, etc.). The continuous phase of such a copolymer can be, for example, polyglycolide, polylactide, lactide-glycolide copolymers, etc. Provided they have adequate melt viscosity properties, polymeric wire can be formed using conventional extrusion and fiber drawing techniques. These polymeric wires can then be bent and formed into staples.

It has also been found that blends of polymers can be used to form surgical staples. The blends can consist of absorbable or nonabsorbable polymers or copolymers or combinations thereof. For example, it is known (U.S. Pat. No. 3,005,795) that small amounts of finely divided microfibrous polytetrafluoroethylene will improve extrusion properties by increasing the melt viscosity of otherwise too fluid polymers. The second phase may also provide enhanced toughness to the polymeric wire.

The ductility of the polymeric wires may also make it possible to form other types of devices. One such device is a "twist tie" as is commonly used for holding objects together. The "twist" can be used in place of a knot. This could be of great use in noninvasive surgery techniques in use today where knot tying may be difficult.

The invention is further described in the following examples:

EXAMPLE 1

General Polymerization Procedure for 1-Lactide Homopolymers

1-Lactide, diethylene glycol (DEG), and stannous octoate were combined and melted under a nitrogen atmosphere. The mixture was charged into a nitrogen purged stirred reactor at 200° C. The contents were maintained at this temperature until maximum melt viscosity was achieved. The polymer was discharged from the reactor, ground and dried in a vacuum oven for 12–18 hours at 100° C. and 0.2 mm Hg. Specific examples of polymers prepared by this procedure are summarized in Table 1.

EXAMPLE 2

General Polymerization Procedure for 1-Lactide-b-TMC Copolymers

Trimethylene carbonate (TMC), diethylene glycol (DEG), and stannous octoate were combined and melted under a nitrogen atmosphere. The mixture was charged into a nitrogen purged stirred reactor at 180° C. The contents were stirred at this temperature until maximum melt viscosity was achieved. 1-Lactide was melted under a nitrogen atmosphere and charged into the reactor. The reactor temperature was increased to 195° C. over a 15 minute period. The contents were maintained at this temperature until maximum melt viscosity was obtained. The polymer was discharged from the reactor, ground and dried in a vacuum oven for 12–18 hours at 100° C. and 0.2 mm Hg. Specific examples of polymers prepared by this procedure are summarized in Table 2.

EXAMPLE 3

General Polymerization Procedure for l-Lactide-b-Caprolactone Copolymers

ε-caprolactone (CAP), diethylene glycol (DEG), and stannous octoate were combined and melted under a nitrogen atmosphere. The mixture was charged into a nitrogen purged stirred reactor at 200° C. The contents were stirred at this temperature until maximum melt viscosity was achieved. l-Lactide was melted under a nitrogen atmosphere and charged into the reactor. The contents were maintained at 200° C. until maximum melt viscosity was obtained. The polymer was discharged from the reactor, ground and dried in a vacuum oven for 12–18 hours at 100° C. and 0.2 mm Hg. Specific examples of polymers prepared by this procedure are summarized in Table 3.

EXAMPLE 4

General Polymerization Procedure for Glycolide Homopolymers

Glycolide (Gly), lauryl alcohol (LA), and stannous chloride dihydrate were combined and melted under a nitrogen atmosphere. The mixture was charged into a nitrogen purged stirred reactor at 180° C. The temperature was increased to 225° C. over a 45 minute period. The contents were maintained at 225° C. until maximum melt viscosity was achieved. The polymer was discharged from the reactor, ground and dried in a vacuum oven for 12–18 hours at 100° C. and 0.2 mm Hg. Specific examples of polymers prepared by this procedure are summarized in Table 4.

EXAMPLE 5

General Polymerization Procedure for Glycolide-b-TMC Copolymers

Trimethylene carbonate (TMC), diethylene glycol (DEG), and stannous chloride dihydrate were combined and melted under a nitrogen atmosphere. The mixture was charged into a nitrogen purged stirred reactor at 170° C. The contents were stirred at this temperature until maximum melt viscosity was achieved. Glycolide was melted under a nitrogen atmosphere and charged into the reactor. The temperature was increased to 225° C. over a 15 minute period and the contents maintained at 225° C. until maximum melt viscosity was obtained. The polymer was discharged from the reactor, ground and dried in a vacuum oven for 12–18 hours at 100° C. and 0.2 mm Hg. Specific examples of polymers prepared by this procedure are summarized in Table 5.

EXAMPLE 6

Polymerization Procedure for Glycolide-l-Lactide Copolymers l-Lactide (l-Lac) (174.36 g), Glycolide (Gly) (1.66 g) and stannous octoate (50.0 mg) were combined and melted under a nitrogen atmosphere. The mixture was charged into a nitrogen purged stirred reactor at 180° C. The contents were stirred at this temperature for 80 minutes, at which point maximum melt viscosity was achieved. The temperature was then raised to 225° C. over a 15 minute period. When this temperature was reached glycolide, which had been melted under a nitrogen atmosphere was charged into the reactor. The contents were then stirred at 225° C. for 12 minutes. The polymer was discharged from the reactor, ground and dried in a vacuum oven for 12–18 hours at 100° C. and 0.2 mm Hg. Specific examples of polymers prepared by this procedure are summarized in Table 6.

EXAMPLE 7

General Polymerization Procedure for Glycolide-b-Caprolactone Copolymers

ε-caprolactone (Cap), diethylene glycol (DEG), and stannous octoate were combined and melted under a nitrogen atmosphere. The mixture was charged into a nitrogen purged stirred reactor at 200° C. The contents were stirred at this temperature until maximum melt viscosity was achieved. Glycolide was melted under nitrogen and charged into the reactor. The temperature was increased to 225° C. over a 15 minute period, and the contents maintained at 225° C. until maximum melt viscosity was obtained. The polymer was discharged from the reactor, ground and dried in a vacuum oven for 12–18 hours at 100° C. and 0.2 mm Hg. Specific examples of polymers prepared by this procedure are summarized in Table 7.

EXAMPLE 8

Extruded and Drawn Polymeric Wires

Extrusion of l-Lactide Rich Polymeric Wires

Polymeric wires of different diameters to be used for test specimen preparation were extruded and drawn in the following manner. The polymer was dried in a vacuum oven prior to being added to the hopper of an extruder with a preheated barrel. It was extruded through a single jet with a diameter of 0.120 inch. The extrudate was quenched in 25° C. water at a distance of approximately 3 inches from the jet. The extrudate was then drawn in two stages while the strand was passing through two 4 foot long, circulating hot air ovens. The drawn polymeric wire was collected on a 3.5 inch diameter spool and stored in a dry environment. The specific extrusion conditions for the polymers of Examples 1, 2, 3 and 6 are shown in Table 8a. Some of the polymeric wires were redrawn in a secondary process as indicated in Table 8a. All of the l-lactide based polymeric wires listed in Table 8a and 8b were found to undergo ductile deformation when bent at room temperature.

Extrusion of Polymeric Wires Composed of Glycolide Homopolymer

Polymeric wires of different diameters to be used for test specimen preparation were extruded and drawn in the following manner. The polymer was dried in a vacuum oven prior to being added to the hopper of an extruder with a preheated barrel. It was extruded through a single jet with a diameter of 0.085 inch. The extrudate was quenched in 25° C. water at a distance of approximately 0.75 inches from the jet. The extrudate was then drawn in two stages while the strand was passing through two 10 foot long, circulating hot air ovens. The drawn polymeric wire was collected on a 3.5 inch diameter spool and stored in a dry environment. The specific extrusion conditions for the polymer of Example 4 are shown in Table 8a. All of the glycolide homopolymer based polymeric wires listed in Table 8a and 8b were found to undergo ductile deformation when bent at room temperature.

Extrusion of Polymeric Wires Composed of Glycolide-Trimethylene Carbonate Copolymers A polymeric wire of approximately 0.018 inch diameter to be used for test specimen preparation was extruded and drawn in the following manner. The polymer (example 5) was dried in a vacuum oven prior to being added to the hopper of an extruder with a preheated barrel. It was extruded through a single jet with a diameter of 0.060 inch. The extrudate was quenched in 25° C. water at a distance of approximately 3 inches from the jet. The extrudate was then drawn in two stages while the strand was passing through two 4 foot long, circulating hot air ovens. The drawn polymeric wire was collected on a 3.5 inch diameter spool and stored in a dry environment. The specific extrusion conditions for the polymer of Example 5 are shown in Table 8a. The Glycolide-trimethylene carbonate based polymeric wire was found to undergo ductile deformation when bent at room temperature.

Extrusion of Polymeric Wires Composed of Polyethylene Terephthalate (PET) (Goodyear VFR 10313)

Polymeric wires of different diameters to be used for test specimen preparation were extruded and drawn in the following manner. The polymer was dried in a vacuum oven prior to being added to the hopper of an extruder with a preheated barrel. It was extruded through a single jet with a diameter of 0.120 inch. The extrudate was quenched in 25° C. water at a distance of approximately 3 inches from the jet. The extrudate was then drawn in two stages while the strand was passing through two 4 foot long, circulating hot air ovens. The drawn polymeric wire was collected on a 3.5 inch diameter spool and stored in a dry environment. The specific extrusion conditions for this polymer are shown in Table 8a. All of the PET based polymeric wires listed in Table 8a and 8b were found to undergo ductile deformation when bent at room temperature.

Extrusion of Polymeric Wires Composed of Polybutylene Terephthalate (PBT) (Celanex PBT Type 1600A)

A polymeric wire of approximately 0.018 inch diameter to be used for test specimen preparation was extruded and drawn in the following manner. The polymer was dried in a vacuum oven prior to being added to the hopper of an extruder with a preheated barrel. It was extruded through a single jet with a diameter of 0.085 inch. The extrudate was quenched in 50° C. water at a distance of approximately 1 inch from the jet. The extrudate was then drawn in two stages while the strand was passing through two 10 foot long, circulating hot air ovens. The drawn polymeric wire was collected on a 3.5 inch diameter spool and stored in a dry environment. The specific extrusion conditions for this polymer are shown in Table 8a. The PBT based polymeric wire was found to undergo slight ductile deformation when bent at room temperature. Significant rebound, however, was observed.

Extrusion of Polymeric Wires Composed of Polybutester (a Copolymer of Polytetramethylene Glycol and Butylene Terephthalate, DuPont's HYTREL Type 7246)

Commercial sutures, sizes 2, 1, and 0 NOVAFIL® were tested. The polybutester based polymeric wire was found to undergo slight ductile deformation when bent at room temperature. Significant rebound, however, was observed.

Polypropylene (PP) Wire

Commercial sutures, sizes 2, 1, and 0 PROLENE® were tested. The PP based polymeric wire was found to undergo slight ductile deformation when bent at room temperature. Significant rebound, however, was observed.

Extrusion of Polymeric Wires Composed of High Density Polyethylene (HDPE) (0.75 MFR Sclair 59A Natural HDPE)

Polymeric wires of different diameters to be used for test specimen preparation were extruded and drawn in the following manner. The polymer was added to the hopper of an extruder with a preheated barrel. It was extruded through a single jet with a diameter of 0.060 inch. The extrudate was quenched in 25° C. water at a distance of approximately 3 inches from the jet. The extrudate was then drawn in two stages while the strand was passing through two 4 foot long, circulating hot air ovens. The drawn polymeric wire was collected on a 3.5 inch diameter spool. The specific extrusion conditions are shown in Table 8a. The HDPE based polymeric wire was found to undergo some ductile deformation when bent at room temperature. Slow rebounding of the bend was observed to occur.

Dimensional and Mechanical Testing of Polymeric Wires

The diameter, tensile strength, and modulus of the drawn polymeric wires listed in Table 8a were determined in the following manner. The polymeric wire diameter was determined under a specified pressure applied by the presser foot of a gauge. The gauge was of the dead-weight type and equipped with a direct reading dial graduated to 0.002 mm as prescribed by USP XXII 1990 (General Chapters, Physical Tests and Determinations, <861> Sutures—Diameter, pg. 1614). The tensile strength and modulus were determined using an Instron Testing Machine. The mean dimensional measurements and tensile values are reported in Table 8b.

EXAMPLE 9

Molded Plaque of 1-Lactide-Trimethylene Carbonate Copolymer

Polymer from example 2.g was molded into a plaque for test specimen preparation using a heated hydraulic press. At a press temperature of 200° C., about 23 grams of dry polymer granules were pressed in a 4.25 inch by 4.25 inch by 0.062 inch steel frame between Teflon coated release liner fabric at 500 pounds of pressure for 4 minutes followed by a pressure increase to 5000 pounds for 4 minutes. The hot plaques were cooled between chilled aluminum plates. The plaques were removed from the frame and annealed in the press at about 250 pounds (14 psi) pressure.

The material was found to break when bent at room temperature. The flexural properties were measured using ASTM method D790. The modulus was 710,000 psi, the strength at break was 14,000 psi, and the strain at break was 21.6%. No yield point was observed. This example illustrates that without the enhancement in bending ductility provided by forming an oriented wire, the 95/5 l-Lac/TMC material does not yield in flexure. For comparison see example 8, sample 9 which was found to perform well as a staple material.

EXAMPLE 10

Thermal Analysis of Copolymers and Polymers

Samples of the polymers of Examples 1 to 7 and 8 were analysed by differential scanning calorimetry (DSC) using a Perkin Elmer DSC-4 instrument. Scanning conditions were from −40° C. to 240° C. at 20° C. minimum under nitrogen. Melting points (Tm) and enthalpy of fusion ($H_f$) values were determined by scanning material that had been annealed at 110° C. for 16 hours. The glass transition temperatures (Tg) were determined after quenching the specimen from the melt following the first scan. Some of the samples exhibited two Tg's in the temperature region scanned: Tg(1) and Tg(2). The presence of two Tg's indicates the sample has two amorphous phases. The results of the thermal analyses are shown in Table 9. Several fiber samples were analyzed in the same way as the polymer samples. These fiber results are also shown in Table 9.

EXAMPLE 11

Preformed Staple Formation

Staples were shaped and pointed in a manner which is similar to conventional metal staple forming. Only selected lengths of the polymeric wires of Example 8 were used for making preformed staples. The diameter of the chosen polymeric wire lengths was limited to three sizes: 0.021, 0.018, and 0.015 inch (each size ±0.001 inch). The polymeric wire was formed into a U-shape by bending it at room temperature over two radii of approximately 0.010 inch to a 90° angle.

The minimal force to bend the polymeric wire completely around the anvil without damaging it was applied. While the polymeric wire was held against the anvil, each staple point was formed by shearing the polymeric wire at a 45° angle to the long axis of the polymeric wire with a steel cutting blade. The length of each leg of the staple was approximately 0.185 inch. The preformed staple was then released from the anvil. The staples were washed in a 1% solution of Pluronic F-68 (a nonionic surfactant) in water. They were then thoroughly rinsed in deionized water and methanol. The staples were dried at room temperature under vacuum to remove all water and methanol residues. The final preformed staple is shown in FIG. 1.

In its preformed state shown in FIG. 1, the surgical staple or staple blank 10 in accordance with the present invention is generally U-shaped as are conventional staples. The legs 14 are shown in parallel form, which is the conventional configuration for staples placed in a surgical stapler track. However, the surgical staple of this invention after being preformed (and before being placed in the stapler track) may relax such that the legs 14 are oblique to each other. Thus the staple 10 includes a back span 12, two legs 14, and an end point 16 formed at the extreme of each leg 14. The end points are sharply chiseled to cleanly pierce the body organs or tissue to be sutured. However, while the polymeric staple is deformable, the end points may be brittle and can break or crush if pressed against a hard surface.

Figure 2:
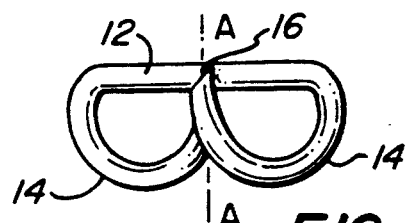
Figure 3:
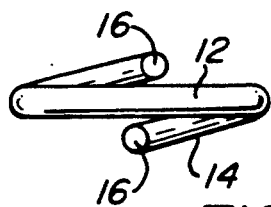
FIG. 3 is a top view of FIG. 2.

FIGS. 2 and 3 show the staple 10 of FIG. 1 in its deformed state. As shown, the legs 14 are bent from their configuration perpendicular (they can also be oblique) to the back span 12 into an arcuate shape with the end points 16 extending toward opposite sides of the back span 12. Thus the brittle end points 16 do not encounter the underside of the back span 12 during deformation, and breaking or crushing of them is mitigated. Preferably, one end point 16 is guided toward one side of the back span and the other end point is guided toward the other side of the back span to further prevent the end points from engaging each other. The end points may desirably be closely adjacent opposite sides of the back span and may extend beyond or past the back span. The end points can also be bent so that each extends in an opposite direction across an axial plan A—A perpendicular to the back span 12 of the staple.

Figure 4:
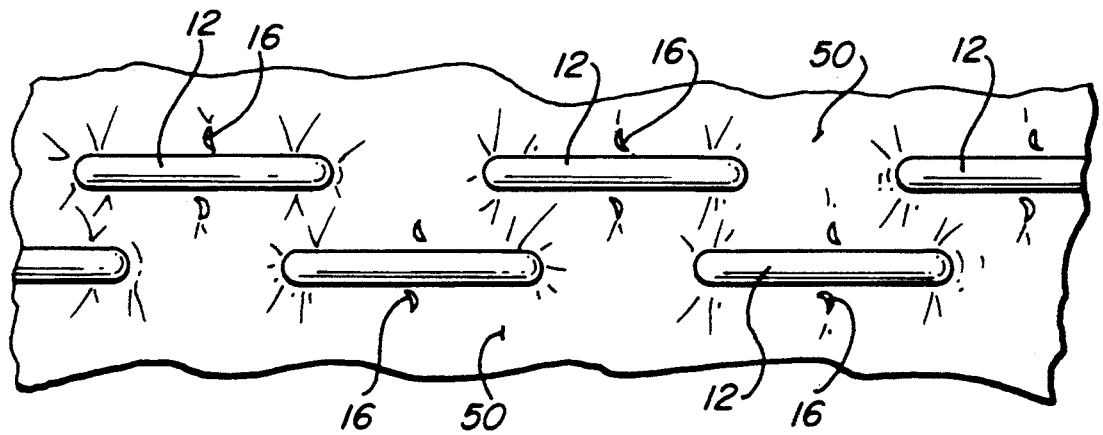
FIG. 4 is a top view showing the sequential in-vivo placement of the staple of FIG. 3.

As shown in FIG. 4, the end points 16 should be guided sufficiently close to the back span 12 so the staple in-vivo body organ 50 cannot work its way off of the end points.

EXAMPLE 12

Measurement of Permanent Bend Angle

A measurement of the permanent deformation after bending the 0.022 inch diameter l-lactide/trimethylene carbonate polymeric wire under staple preform formation conditions was made. This served as a measure of the ductility in bending of the polymeric wire, and can be considered as a test for suitability of a polymeric wire material for use as a staple. The wire was bent over a radius of approximately 0.010 inch to a 90° angle by using the staple forming fixture of example 11. The specimen was removed from the fixture and immediately placed on an optical comparator at a magnification of 50×. The angle between the shaped leg and the backspan was measured. The measurement was repeated 0.5, 1, 4, and 24 hours after the staple was formed. The results are summarized in table 10.

EXAMPLE 13

Sterilization of Preformed Staples 13.a: EtO Sterilization of l-Lac/TMC Polymeric Wires The polymeric staples were packaged in paper support cards which were then inserted into foil laminate envelopes. During this step of the packaging process, the staples were stored overnight in a dry environment. The open foil envelopes and their contents were sterilized by exposure to ethylene oxide (ETO) and then vacuum dried. After vacuum drying, the staples and open foil envelopes were always stored or handled in a dry environment until the foil envelopes were aseptically heat sealed. After outer Tyvek®/Mylar® pouches were applied, the outside surfaces of the foil envelopes were sterilized by exposure to ethylene oxide. Staples formed from polymeric wire from example 8, sample 4 were sterilized by ETO for testing.

13.b–d: Radiation Sterilization of l-Lac/TMC Polymeric Wires

In a dry environment, the polymeric staples formed from the polymeric wire from example 8, sample 4, were packaged in predried paper support cards which were then inserted into predried foil laminate envelopes. The foil envelopes were heat sealed and packaged in Tyvek/Mylar outer pouches. The finished packages were sterilized via Cobalt 60 radiation at doses of 2.5 Mrad minimum to 3.0 Mrad maximum (example 13.b) or 5.0 Mrad minimum to 7.0 Mrad maximum (examples 13.c and 13.d).

13.e–g: Radiation Sterilization of 1-Lac/Cap Polymeric Wires

In a dry environment, the polymeric staples formed from the polymeric wire from example 8, samples 10, 11 and 12, were packaged in predried paper support cards which were then inserted into predried foil laminate envelopes. The foil envelopes were heat sealed and packaged in Tyvek/Mylar outer pouches. The finished packages were sterilized via Cobalt 60 radiation at doses of 2.5 Mrad minimum to 3.0 Mrad maximum. The sterile staples from example 8, samples 10, 11 and 12 were designated examples 13.e, 13.f and 13.g respectively.

EXAMPLE 14

Formation and Testing of Formed Staples

Staple Formation

Figure 5:
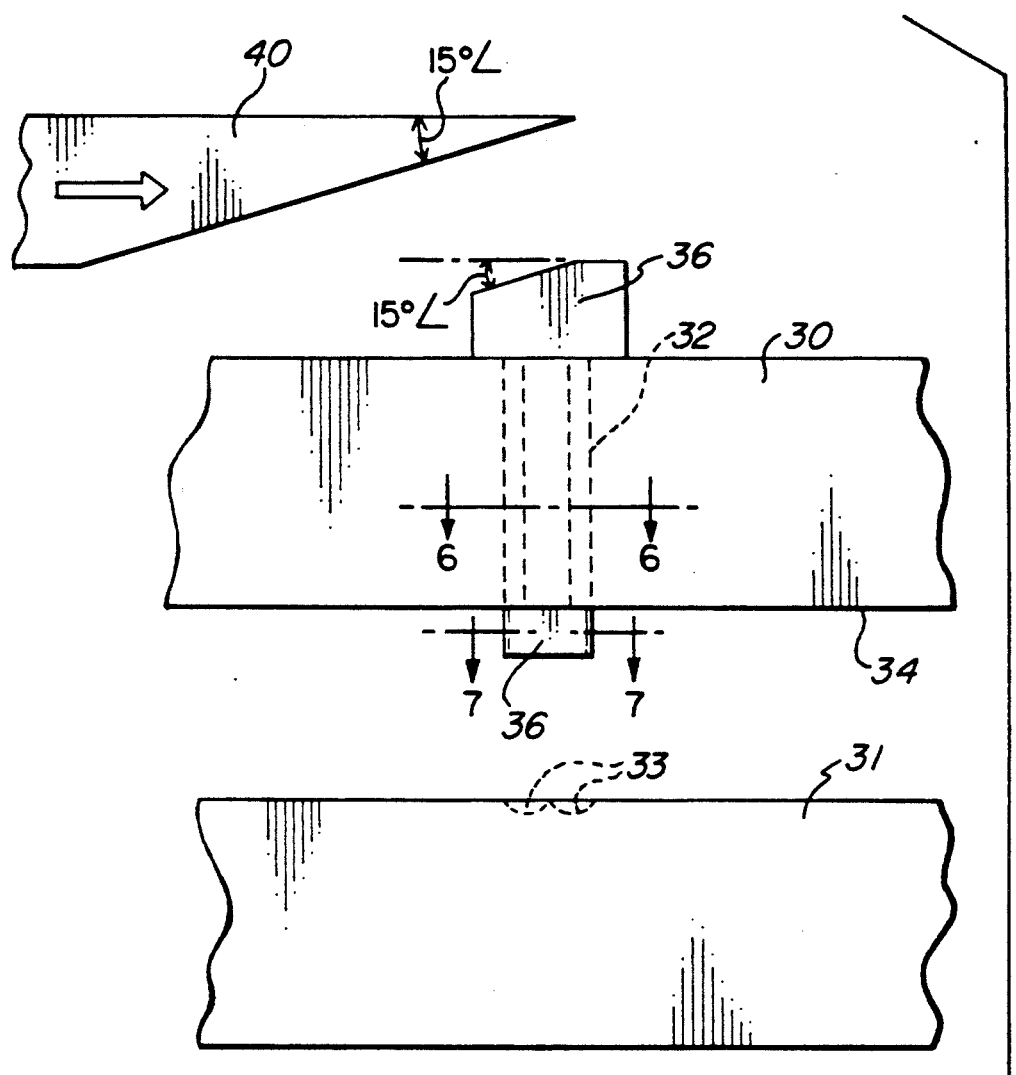
FIG. 5 is a partial side view showing apparatus for deforming the staple of FIG. 2.

The preformed staples of Example 11 could be implanted into various materials by using a delivery system which operated similarly to a metal stapler. Referring to FIG. 5, the delivery system consisted of two mating halves—a cartridge 30 and an anvil 31. Each preformed staple (shown in FIG. 1) was loaded into a slot 32 in the cartridge such that the staple legs would be pushed against the anvil when the tool was activated. The anvil consisted of a number of specially designed pockets 33 which bent the staple legs as the staple was moved forward through the cartridge. A description of anvil pockets which can be used in this application is more fully described in related U.S. application Ser. No. 07/785,295 filed Oct. 30, 1991 entitled "Malleable, Bioabsorbable, plastic Staple; And Method And Apparatus For Deforming Such Staple", which is incorporated herein by reference. The anvil pockets were designed so that the staple points, after passing through the pocket, would pass by the staple backspan on opposite sides. A single formed staple is shown in FIG. 2 and 3.

The delivery device had a sufficient number of slots 32 and anvil pockets 33 to form two rows of staples approximately 1 inch in length as shown in FIG. 4. Staple rows of this type are commonly used to suture parenchymal organs.

Figure 7:
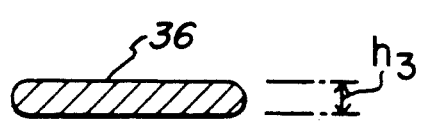
FIGS. 6 and 7 are partial cutaway views on the respective planes 6—6 and 7—7 of FIG. 5.
Figure 6:
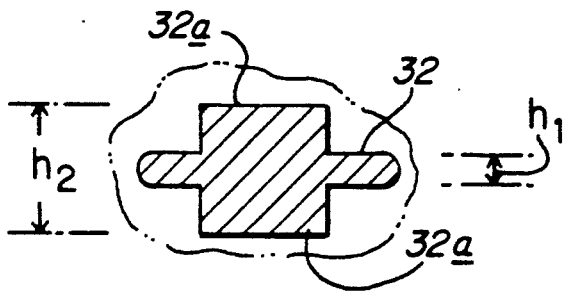

The gap between the bottom surface 34 of the cartridge and the anvil was 0.040 in. The slot length (more fully shown in FIG. 6) was 0.166 in. Referring to FIG. 6, the slot extensions 32a accommodate the staple ends 16 (shown in FIGS. 2 and 3) if they pass over the top of the back span 12. The height $h_1$ is about 0.005 inches greater than the diameter of the chosen polymeric wire (see, e.g., example 11 above). The height $h_2$ is approximately equal to three times $h_1$. Referring again to FIG. 5, the pusher 36 (more fully shown in FIG. 7) fits snugly into the slot and has a squared-off, flat end to provide uniform pressure across the back span 12 (shown in FIG. 1) during the forming stroke. Referring to FIG. 7, the height $h_3$ is approximately equal to the diameter of the chosen polymeric wire described in example 11 above. The length of the slot 32 and the pusher 36 (with the pusher length being about 0.005 inches less than the slot length) is approximately equal to the length of the back span 12, shown e.g. in FIG. 3.

At the completion of the staple formation stroke, the pusher 36 extended 0.010 in. beyond the slot opening 32 into the gap. A slide bar 40 was used to move the pusher 36 during the staple formation stroke.

Staple Opening Strength Testing

The opening strength of the staple was determined in the following manner. A single staple was loaded into the delivery system and formed through two layers of polyethylene (each 0.004 in T×1.0 in W×5 in L). The staple was centered in the polyethylene strips and the backspan of the staple was perpendicular to the long axis of the strips. The same anvil pocket was used to form each staple. These specimens were tested before conditioning or after a specified in vitro conditioning period (7, 14, 21, 28, 35, or 42 days in 6.09 pH, 37±0.2_C buffer solution). The mechanical testing was performed using an Instron Testing Machine. The strength of each staple was determined by folding each polyethylene sheet back on itself and gripping the ends such that the two legs of the staple would open evenly when the Instron crosshead was activated. The maximum load recorded during the test was defined as the opening strength of the staple. The results of the mechanical testing are summarized in Table 11.

EXAMPLE 15

Preclinical Testing

Using aseptic technique, an end-to-end, everting anastomosis (Stapling in Surgery, Steichen and Ravitch, p. 274) of the small bowel of a beagle was performed using a prototype delivery device (See example 14) and ethylene oxide sterilized staples of 0.022 inch diameter 80/20 1-lactide/trimethylene carbonate wire (example 13.b). A second end-to-end, everting anastomis was performed approximately 14 inches away in the bowel using a commercially available internal stapler which delivered a double row of 0.009 inch diameter stainless steel staples (Auto Suture ® TA-55 Surgical Stapler, United States Surgical Corp., Norwalk, Ct.). Prior to closing the wound, saline was injected into the bowel proximal to each anastomosis, demonstrating patency and water tightness. The laparotomy was closed using standard technique. The dog was euthanized 8 days postoperatively in order to evaluate the two anastomoses.

Gross examination of the anastomoses, both the polymeric and metal staple procedures, revealed that they were patent and nonstenotic. Healing appeared to be progressing normally. For each anastomosis, a segment of the bowel containing the operative site was removed and burst hydraulically. The 8 day polymeric staple anastomosis burst at 420 mm Hg, and the 8 day metal staple anastomosis burst at 400 mm Hg. All specimens were then opened longitudinally, trimmed and examined. The mucosal surfaces appeared similar at the polymeric and metal staple anastomoses.

EXAMPLE 16

Creep Testing of Formed Staples

Figure 8:
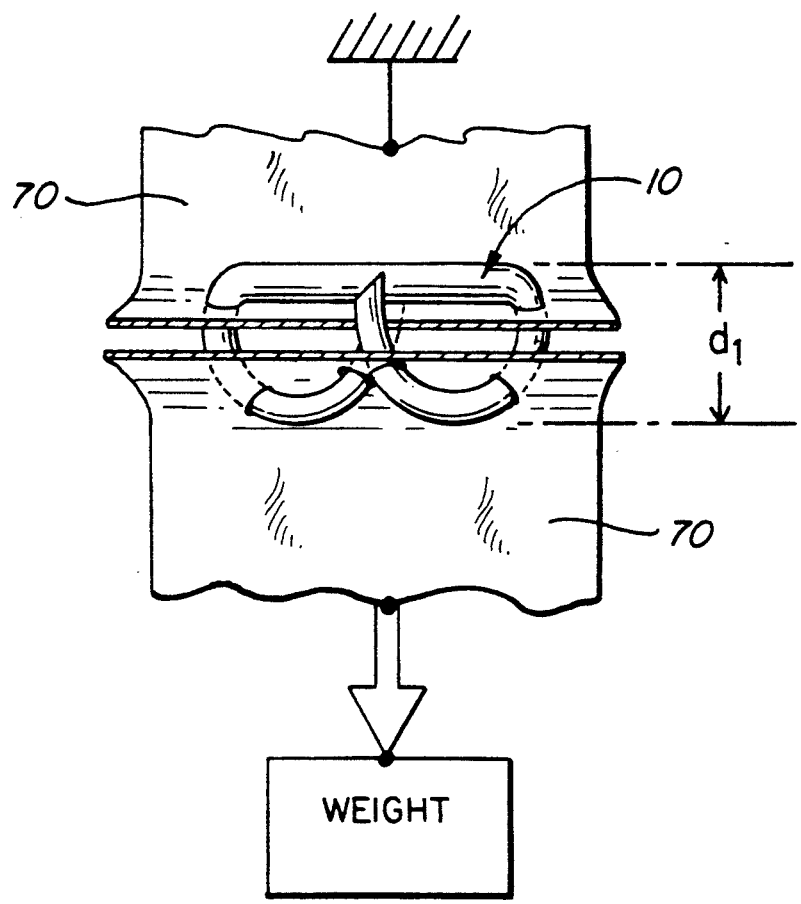
FIG. 8 is a cutaway side view showing the creep testing of the staple deformed by FIG. 5.

As shown in FIG. 8, a staple 10 formed from 0.022 inch diameter lactide/TMC polymeric wire (Table 8a, sample 4) were subjected to two different weights while immersed in 37° C. normal saline. The displacement $d_1$ of the staple legs was measured for up to 17 days.

Each staple 10 was formed through two 0.002 inch thick Mylar ® films 70. Each film of Mylar was folded back upon itself, and a weight (72 g or 50 g in air) was attached to the lower half of the test. The specimens were then hung in a tank of 37° C. normal saline. The distance from top of the staple back span 12 to the bottom of the staple leg 14 was measured using a camera and a video micro scaler system. Measurements were taken at 2 minutes (baseline), 1 hour, and 1, 3, 6, 8, 11, 13, 14, and 17 days. After 17 days, the specimens were carefully removed from the tank, and the breaking strength of the staples was determined on an Instron testing machine.

Figure 9:
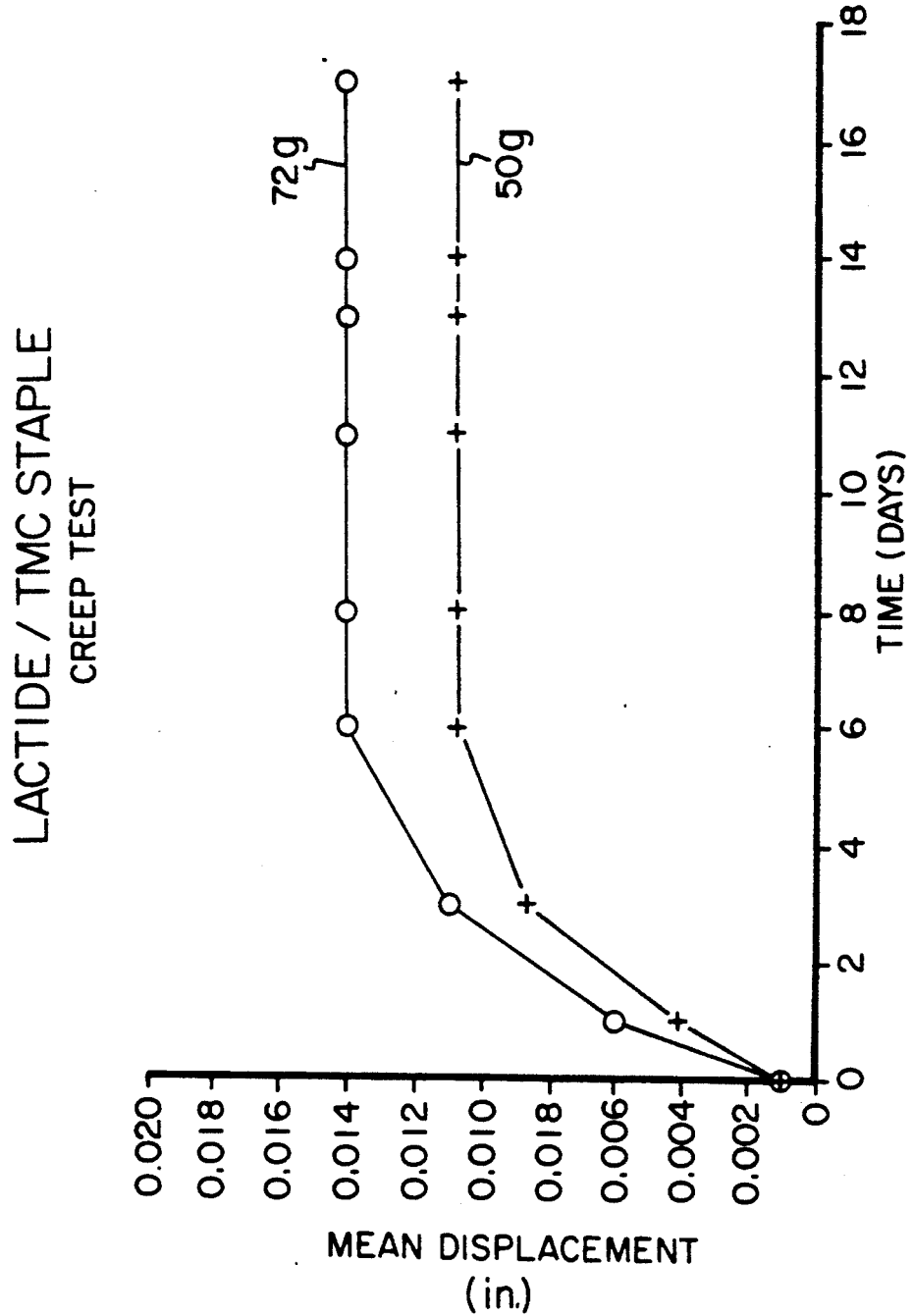
FIG. 9 is a graph showing the creep test results of FIG. 8 versus time.

The results of the creep test are summarized in Table 12. The mean displacement with time is also shown graphically in FIG. 9. The mean displacement of the specimens with the 72 g weight increased to 0.014 inch (18% of baseline staple height) at 6 days and then remained constant up to 17 days. For the specimens with the 50 g weight, the mean displacement increased to 0.011 inch (14%) at 6 days, and then remained constant up to 17 days.

After creep testing, the opening strengths of the test specimens were determined as described in example 14. The overall mean opening strength of the staples was 686 grams (674 g for the 72 gram test and 698 g for the 50 gram test).

TABLE 1

Poly(l-Lactide Homopolymers)

| Example | Charged Composition | | | | | Polymerization Time (Hr:Min) | Analyzed Composition | |
|---|---|---|---|---|---|---|---|---|
| | l-Lactide (grams) | DEG[1] (mg) | (mole %)[2] | Stannous octoate (mg) | (mole %)[2] | | l-Lactide (mole %)[3] | IV (CHCl3)[4] |
| 1.a | 230.0 | 8.5 | 0.005 | 19.4 | 0.003 | 2:26 | 100 | 1.76 |
| 1.b | 230.0 | 8.5 | 0.005 | 19.4 | 0.003 | 1:28 | 100 | 1.90 |
| 1.c | 230.0 | 8.5 | 0.005 | 19.4 | 0.003 | 1:52 | 100 | 1.79 |
| 1.d | 250.0 | 239 | 0.130 | 21.1 | 0.003 | 3:25 | 100 | 1.34 |

[1]DEG = diethylene glycol.
[2]Based on moles of l-lactide.
[3]Determined by $^1$H-Nuclear Magnetic Resonance spectroscopy. In all cases the level of residual monomer was found to be <0.5 wt %.
[4]Inherent Viscosity, measured in Chloroform at 30° C., polymer concentration = 0.5 g/dL.

TABLE 2

Poly(l-Lactide-b-TMC)

| Example | Charged Composition | | | | | | Polymerization Time (Hr:Min) Reaction Stage | | Analyzed Composition | |
|---|---|---|---|---|---|---|---|---|---|---|
| | l-Lac/TMC (grams) | (mole %) | DEG[1] (mg) | (mole %)[2] | Stannous octoate (mg) | (mole %)[2] | 1 | 2 | l-Lac/TMC (mole %)[3] | IV (CHCl3)[4] |
| 2.a | 199.95/35.40 | 80/20 | 239 | 0.13 | 21.1 | 0.003 | 1:25 | 1:09 | 77.1/22.9 | 1.21 |
| 2.b | 225.00/17.66 | 90/10 | 239 | 0.13 | 21.1 | 0.003 | 1:34 | 0:57 | 90.1/9.9 | 1.31 |
| 2.c | 5944/1056 | 80/20 | 490 | 0.01 | 505 | 0.003 | 0:45 | 3:30 | 79.2/20.8 | 1.50 |
| 2.d | 212.46/26.54 | 85/15 | 18.4 | 0.01 | 21.1 | 0.003 | 1:24 | 1:56 | 85.3/14.7 | 1.91 |
| 2.e | 225.00/17.66 | 90/10 | 18.4 | 0.01 | 21.1 | 0.003 | 0:24 | 2:25 | 90.1/9.9 | 1.93 |
| 2.f | 237.50/8.88 | 95/5 | 18.4 | 0.01 | 21.1 | 0.003 | 0:25 | 2:54 | 94.7/5.3 | 1.71 |
| 2.g | 205.34/7.66 | 95/5 | 16.9 | 0.01 | 18.2 | 0.003 | 0:21 | 3:40 | 95.3/4.7 | 1.65 |

[1]DEG = diethylene glycol.
[2]Based on moles of l-Lactide plus TMC.
[3]Determined by $^1$H-Nuclear Magnetic Resonance spectroscopy. In all cases residual monomer was <0.5 wt %.
[4]Inherent viscosity, measured in Chloroform at 30° C., polymer concentration = 0.5 g/dL.

TABLE 3

Poly(Caprolactone-l-Lactide)

| Example | Charged Composition | | | | | | Polymerization Time (Hr:Min) Reaction Stage | | Analyzed Composition | |
|---|---|---|---|---|---|---|---|---|---|---|
| | l-Lac/Cap (grams) | (mole %) | DEG[1] (mg) | (mole %)[2] | Stannous octoate (mg) | (mole %)[2] | 1 | 2 | l-Lac/Cap (mole %)[3] | IV (CHCl3)[4] |
| 3.a | 201.35/35.00 | 80/20 | 18.1 | 0.01 | 20.7 | 0.003 | 1:03 | 2:07 | 81.9/18.2 | 1.80 |
| 3.b | 170.38/29.62 | 80/20 | 15.3 | 0.01 | 17.3 | 0.003 | 1:03 | 1:59 | 81.4/18.6 | 1.76 |
| 3.c | 170.38/29.62 | 80/20 | 15.3 | 0.01 | 17.3 | 0.003 | 0:48 | 2:45 | 80.6/19.4 | 1.69 |
| 3.d | 170.38/29.62 | 80/20 | 15.3 | 0.01 | 17.3 | 0.003 | 0:48 | 2:50 | 81.1/18.9 | 1.84 |
| 3.e | 213.75/11.25 | 95/5 | 16.6 | 0.01 | 19.0 | 0.003 | 0:38 | 2:54 | 94.1/5.9 | 1.74 |
| 3.f | 213.75/11.25 | 95/5 | 16.6 | 0.01 | 19.0 | 0.003 | 0:28 | 3:00 | 93.6/6.4 | 1.74 |

[1]DEG = Diethylene glycol.
[2]Based on moles of l-Lactide plus Cap.
[3]Determined by $^1$H-Nuclear Magnetic Resonance spectroscopy. In all cases residual monomer was <0.5 wt %.
[4]Inherent viscosity, measured in Chloroform at 30° C., polymer concentration = 0.5 g/dL.

TABLE 4

Poly(glycolide)Homopolymers

| Example | Charged Composition | | | | | Polymerization Time (Hr:Min) | Analyzed Composition | |
|---|---|---|---|---|---|---|---|---|
| | Glycolide (grams) | LA[1] mg | (mole %)[2] | $SnCl_2 \cdot 2H_2O$ mg | (mole %)[2] | | Glycolide (mole %)[3] | IV (HFAS)[4] |
| 4.a | 250.00 | 20.1 | 0.005 | 2.4 | 0.0005 | 2:19 | 100 | 1.06 |

TABLE 4-continued

| | | | | | | | | |
|---|---|---|---|---|---|---|---|---|
| 4.b | 250.00 | 20.1 | 0.005 | 2.4 | 0.0005 | 4:30 | 100 | 0.95 |

[1]LA = lauryl alcohol.
[2]Based on moles of glycolide.
[3]Measured by [1]H-Nuclear Magnetic Resonance spectroscopy. In all cases residual monomer was <0.5 wt %.
[4]Inherent viscosity, measured in hexafluoroacetonesesquihydrate at 30° C., polymer concentration = 0.5 g/dL.

TABLE 5

Poly(glycolide-b-TMC)

| | Charged Composition | | | | | | Polymerization Time (Hr:Min) Reaction Stage | | Analyzed Composition | |
|---|---|---|---|---|---|---|---|---|---|---|
| | Gly/TMC | | DEG[1] | | SnCl₂.2H₂O | | | | Gly/TMC | IV |
| Example | (grams) | (mole %) | (mg) | (mole %)[2] | (mg) | (mole %)[2] | 1 | 2 | (mole %)[3] | (HFAS)[4] |
| 5.a | 30005/14449 | 67/33 | 2795 | 0.007 | 1044 | 0.001 | 0:39 | 1:29 | 65.7/34.3 | 0.95 |
| 5.b | 181.91/40.00 | 80/20 | 4.2 | 0.002 | 4.4 | 0.001 | 0:30 | 1:27 | 81.6/18.4 | 1.05 |
| 5.c | 181.91/40.00 | 80/20 | 4.2 | 0.002 | 4.4 | 0.001 | 0:26 | 1:20 | 81.9/18.1 | 0.99 |
| 5.d | 181.91/40.00 | 80/20 | 4.2 | 0.002 | 4.4 | 0.001 | 0:25 | 1:20 | 81.9/18.1 | 1.00 |

[1]DEG = diethylene glycol.
[2]Based on moles of Glycolide plus trimethylene carbonate.
[3]Measured by [1]H-Nuclear Magnetic Resonance spectroscopy, in all cases residual monomer was found to be <0.5 wt %.
[4]Inherent Viscosity, measured in hexafluoroacetonesesquihydrate at 30° C., polymer concentration = 0.5 g/dL.

TABLE 6

Poly(Glycolide-1-Lactide)Polymers

| | Charged Composition | | | | Polymerization Time (Hr:Min) Reaction Stage | | Analyzed Composition | |
|---|---|---|---|---|---|---|---|---|
| | 1-Lactide/Gly | | SnCl₂.2H₂O | | | | 1-Lac/Gly | IV |
| Example | (grams) | (mole %) | (mg) | (mole %)[1] | 1 | 2 | (mole %)[2] | (HFAS)[3] |
| 6.a | 174.36/61.69 | 71/29 | 50.0 | 0.013 | 1:31 | 0:12 | 67.3/32.7 | 1.30 |
| 6.b | 174.36/61.69 | 71/29 | 50.0 | 0.013 | 1:32 | 0:14 | 64.1/35.9 | 1.12 |

[1]Based on moles Glycolide plus 1-Lactide.
[2]Measured by [1]H-Nuclear Magnetic Resonance spectroscopy. In all cases residual monomer was found to be <0.5 wt %.
[3]Inherent Viscosity, measured in hexafluoroacetonesesquihydrate at 30° C., polymer concentration = 0.5 g/dL.

TABLE 7

Poly(Glycolide-b-Caprolactone)Copolymers

| | Charged Composition | | | | | | Polymerization Time (Hr:Min) Reaction Stages | | Analyzed Composition | |
|---|---|---|---|---|---|---|---|---|---|---|
| | Gly/Cap | | DEG[1] | | SnCl₂.2H₂O | | | | Gly/Cap | IV |
| Example | (grams) | (mole %) | (mg) | (mole %)[2] | (mg) | (mole %)[2] | 1 | 2 | (mole %)[3] | (HFAS)[4] |
| 7.a | 180.00/45.00 | 80/20 | 20.6 | 0.010 | 39.4 | 0.005 | 0:44 | 0:35 | 81.9/18.1 | 1.26 |
| 7.b | 180.00/45.00 | 80/20 | 20.6 | 0.010 | 39.4 | 0.005 | 0:22 | 0:31 | 80.6/19.4 | 1.40 |
| 7.c | 180.00/45.00 | 80/20 | 20.6 | 0.010 | 39.4 | 0.005 | 0:20 | 0:28 | 80.6/19.4 | 1.35 |

[1]DEG = diethylene glycol.
[2]Based on moles Glycolide plus Caprolactone.
[3]Measured by [1]H-Nuclear Magnetic Resonance spectroscopy. In all cases residual monomer was found to be <0.5 wt %.
[4]Inherent Viscosity, measured in hexafluoroacetonesesquihydrate at 30° C., polymer concentration = 0.5 g/dL.

TABLE 8a

Polymeric Wire Extrusion Conditions

| Polym. wire sample | Polymer From Example | Polymer | Final Diameter (mm) | Head Temp. (°C.) | 1st Draw Ratio | 1st Oven Temp (°C.) | 2nd Draw Ratio | 2nd Oven Temp (°C.) | Redraw Draw Ratio | Redraw Oven Temp (°C.) |
|---|---|---|---|---|---|---|---|---|---|---|
| 1 | 1.a-c | poly(1-lactide) | 0.522 | 220 | 4.91 | 107 | 1.09 | 115 | | |
| 2 | 1.a-c | poly(1-lactide) | 0.454 | 220 | 5.48 | 107 | 1.10 | 107 | | |
| 2 | 1.a-c | poly(1-lactide) | 0.383 | 220 | 6.04 | 108 | 1.11 | 116 | | |
| 4 | 2.c | 80/20 lactide/TMC | 0.548 | 225 | 5.22 | 95 | 1.11 | 115 | 1.23 | 114 |
| 5 | 2.c | 80/20 lactide/TMC | 0.444 | 225 | 5.20 | 95 | 1.10 | 133 | 1.66 | 125 |
| 6 | 2.c | 80/20 lactide/TMC | 0.415 | 225 | 6.15 | 99 | 1.08 | 134 | 1.23 | 115 |
| 7 | 2.d | 85/15 lactide/TMC | 0.538 | 215 | 5.33 | 98 | 1.08 | 117 | 1.25 | 111 |
| 8 | 2.e | 90/10 lactide/TMC | 0.544 | 221 | 5.30 | 96 | 1.13 | 116 | 1.22 | 110 |
| 9 | 2.f | 95/5 lactide/TMC | 0.541 | 230 | 5.34 | 94 | 1.13 | 115 | 1.22 | 111 |
| 10 | 3.c-d | 80/20 lactide/cap | 0.557 | 215 | 5.68 | 89 | 1.09 | 100 | | |
| 11 | 3.c-d | 80/20 lactide/cap | 0.467 | 216 | 5.94 | 89 | 1.10 | 99 | | |
| 12 | 3.c-d | 80/20 lactide/cap | 0.394 | 216 | 5.73 | 90 | 1.10 | 99 | | |
| 13 | 3.e-f | 95/5 lactide/cap | 0.529 | 217 | 5.29 | 98 | 1.13 | 111 | | |
| 14 | 3.e-f | 95/5 lactide/cap | 0.484 | 215 | 5.64 | 100 | 1.11 | 113 | | |
| 15 | 3.e-f | 95/5 lactide/cap | 0.374 | 215 | 5.76 | 100 | 1.11 | 113 | | |
| 16 | 4.a-b | Polyglycolide | 0.539 | 249 | 5.43 | 65 | 1.00 | 149 | | |
| 17 | 4.a-b | Polyglycolide | 0.457 | 248 | 5.45 | 65 | 1.00 | 149 | | |
| 18 | 4.a-b | Polyglycolide | 0.385 | 249 | 6.23 | 60 | 1.10 | 111 | | |

TABLE 8a-continued

| | | | | Polymeric Wire Extrusion Conditions | | | | | | |
|---|---|---|---|---|---|---|---|---|---|---|
| Polym. wire sample | Polymer From Example | Polymer | Final Diameter (mm) | Head Temp. (°C.) | 1st Draw Ratio | 1st Oven Temp (°C.) | 2nd Draw Ratio | 2nd Oven Temp (°C.) | Redraw Draw Ratio | Redraw Oven Temp (°C.) |
| 19 | 4.a-b | Polyglycolide | 0.381 | 248 | 5.44 | 65 | 1.00 | 149 | | |
| 20 | 5.a | 67/33 glycolide/TMC | 0.494 | 217 | 5.75 | 49 | 1.22 | 56 | | |
| 21 | 6.a-b | 25/75 glycolide/l-lac | 0.641 | 215 | 4.21 | 92 | 1.14 | 113 | | |
| 22 | 6.a-b | 25/75 glycolide/l-lac | 0.582 | 215 | 5.11 | 87 | 1.11 | 113 | | |
| 23 | 6.a-b | 25/75 glycolide/l-lac | 0.385 | 215 | 5.55 | 89 | 1.09 | 113 | | |
| 24 | | PET | 0.442 | 277 | 5.30 | 77 | 1.01 | 138 | | |
| 25 | | PET | 0.374 | 278 | 5.42 | 73 | 1.02 | 142 | | |
| 26 | | PET | 0.368 | 279 | 5.45 | 82 | 1.02 | 141 | | |
| 27 | | PBT | 0.477 | 250 | 4.00 | 180 | 1.25 | 180 | | |
| 28 | | HDPE | 0.525 | 201 | 8.68 | 122 | 1.11 | 124 | | |
| 29 | | HDPE | 0.491 | 201 | 8.85 | 87 | 1.11 | 101 | | |
| 30 | | HDPE | 0.478 | 200 | 10.11 | 110 | 1.11 | 110 | | |
| 31 | | HDPE | 0.439 | 200 | 9.43 | 123 | 1.11 | 127 | | |
| 32 | | HDPE | 0.381 | 201 | 10.00 | 124 | 1.11 | 127 | | |
| 33 | | Polybutester | 0.598 | Commercially available suture | | | | | | |
| 34 | | Polybutester | 0.492 | Commercially available suture | | | | | | |
| 35 | | Polybutester | 0.381 | Commercially available suture | | | | | | |
| 36 | | PP | 0.487 | Commercially available suture | | | | | | |
| 37 | | PP | 0.468 | Commercially available suture | | | | | | |
| 38 | | PP | 0.381 | Commercially available suture | | | | | | |

TABLE 8b

POLYMERIC WIRE MECHANICAL PROPERTIES

| Polym. Wire Sample | Polymer From Example | Polymer | Diameter (mm) | Modulus ($10^3$ psi) | At Break Strength ($10^3$ psi) | At Break Strain (%) |
|---|---|---|---|---|---|---|
| 1 | 1.a-c | poly(l-lactide) | 0.522 | 1047 | 54.0 | 28.3 |
| 2 | 1.a-c | poly(l-lactide) | 0.454 | 1102 | 63.0 | 26.7 |
| 3 | 1.a-c | poly(l-lactide) | 0.383 | 1066 | 59.9 | 23.0 |
| 4 | 2.c | 80/20 lactide/TMC | 0.548 | 991 | 51.2 | 21.5 |
| 5 | 2.c | 80/20 lactide/TMC | 0.444 | 1061 | 59.7 | 20.2 |
| 6 | 2.c | 80/20 lactide/TMC | 0.415 | 1074 | 53.9 | 19.8 |
| 7 | 2.d | 85/15 lactide/TMC | 0.538 | 1048 | 58.9 | 25.7 |
| 8 | 2.e | 90/10 lactide/TMC | 0.544 | 1088 | 60.4 | 23.6 |
| 9 | 2.f | 95/5 lactide/TMC | 0.541 | 1197 | 61.2 | 24.6 |
| 10 | 3.c-d | 80/20 lactide/cap | 0.557 | 821 | 47.8 | 22.6 |
| 11 | 3.c-d | 80/20 lactide/cap | 0.467 | 846 | 53.5 | 21.5 |
| 12 | 3.c-d | 80/20 lactide/cap | 0.394 | 933 | 54.9 | 22.0 |
| 13 | 3.e-f | 95/5 lactide/cap | 0.529 | 1036 | 59.8 | 26.6 |
| 14 | 3.e-f | 95/5 lactide/cap | 0.484 | 1029 | 59.4 | 26.2 |
| 15 | 3.e-f | 95/5 lactide/cap | 0.374 | 1064 | 60.7 | 22.4 |
| 16 | 4.a-b | Polyglycolide | 0.539 | 1519 | 47.0 | 18.3 |
| 17 | 4.a-b | Polyglycolide | 0.457 | 1771 | 60.7 | 19.2 |
| 18 | 4.a-b | Polyglycolide | 0.385 | 1896 | 73.7 | 20.9 |
| 19 | 4.a-b | Polyglycolide | 0.381 | 2053 | 92.2 | 21.9 |
| 20 | 5.a | 67/33 glycolide/TMC | 0.494 | 839 | 49.2 | 11.5 |
| 21 | 6.a-b | 25/75 gly/lac | 0.641 | 766 | 35.9 | 48.7 |
| 22 | 6.a-b | 25/75 gly/lac | 0.582 | 797 | 45.5 | 29.9 |
| 23 | 6.a-b | 25/75 gly/lac | 0.385 | 894 | 50.0 | 26.0 |
| 24 | | PET | 0.442 | 1839 | 91.1 | 12.5 |
| 25 | | PET | 0.374 | 2010 | 98.5 | 9.9 |
| 26 | | PET | 0.368 | 1920 | 103.6 | 9.5 |
| 27 | | PBT | 0.477 | 507 | 55.9 | 27.1 |
| 28 | | HDPE | 0.525 | 999 | 52.2 | 6.0 |
| 29 | | HDPE | 0.491 | 1140 | 54.4 | 6.4 |
| 30 | | HDPE | 0.478 | 1160 | 52.3 | 4.5 |
| 31 | | HDPE | 0.439 | 1203 | 53.3 | 5.8 |
| 32 | | HDPE | 0.381 | 1302 | 56.0 | 4.8 |
| 33 | | Polybutester | 0.598 | 220 | 69.8 | 33.0 |
| 34 | | Polybutester | 0.492 | 305 | 76.7 | 30.9 |
| 35 | | Polybutester | 0.381 | Not tested | | |
| 36 | | PP | 0.487 | 453 | 67.2 | 30.7 |
| 37 | | PP | 0.468 | 428 | 61.7 | 37.6 |
| 38 | | PP | 0.381 | Not tested | | |

TABLE 9

Thermal Analysis Data

| Polym. Wire Sample | Polymer From Example | Polymer | Tg(1) (°C.) | Tg(2) (°C.) | Tm (°C.) | ΔH$_f$ (J/g) | % Cryst.[1] |
|---|---|---|---|---|---|---|---|
| (See Table 8a) | 1a | poly(1-lactide) | 63.2 | | 177.0 | 52.85 | 56.9 |
| | 2a | 80/20 lactide/TMC | −3.4 | 59.8 | 175.3 | 39.39 | 43.0 |
| | 2d | 95/15 lactide/TMC | −9.9 | 60.8 | 174.2 | 46.89 | 50.5 |
| | 2e | 90/10 lactide/TMC | −9.2 | 61.2 | 176.3 | 52.52 | 56.6 |
| | 2f | 95/5 lactide/TMC | −10.4 | 60.8 | 175.7 | 51.87 | 55.9 |
| | 3a | 80/20 lactide/cap | | ca. 60* | 50.4, 173.8 | 5.81, 44.65 | 4.3, 48.1 |
| | 3c | 95/5 lactide/cap | | 63.6 | 49.6, 178.1 | 1.34, 55.25 | 1.0, 59.9 |
| | 4a | poly(glycolide) | | 43.6 | 224.9 | 82.74 | 43.7 |
| | 5a | 67/33 glycolide/TMC | −9.6 | 40.8 | 221.6 | 42.45 | 22.5 |
| | 5b | 80/20 glycolide/TMC | −9.3 | 41.1 | 225.2 | 67.30 | 35.5 |
| | 6a | 25/75 glycolide/1-lac | 45.7 | 62.0 | 167.1 | 33.14 | 35.7 |
| | 7a | 80/20 glycolide/cap | | ca. 45* | 60.6, 225.8 | 11.59, 64.78 | 8.6, 34.2 |
| 24 | | PET | 82.8 | | 249.9 | 51.35 | 36.7 |
| 27 | | PBT | 41.7 | | 224.8 | 55.06 | 39.1 |
| 28 | | HDPE | | | 137.8 | 215.85 | 74.6 |
| 33 | | Polybutester | ** | ** | 216.06 | 57.60 | 40.9 |
| 36 | | PP | −3 | | 154.5 | 106.2 | 64.5 |

*Tg obscured by endotherm, **Unable to determine Tg, ‡Tg below scan range, ¶single amorphous phase, § two crystalline phases
[1]Calculated using ΔH$_f$ values of 100% cyrstalline polymer taken from "Polymer Handbook", Third Edition, J Brandrup and E. H. Immergut, John Wiley and Sons, 1989.

TABLE 10

Bend Angle Measurement of 0.022 inch Diameter Preformed Staples
Retained Bend Angle (degrees)

| Table 8a Sample | Polymer | 0 Hours | | | 0.5 Hours | | | 1 Hour | | | 4 Hours | | | 24 Hours | | |
|---|---|---|---|---|---|---|---|---|---|---|---|---|---|---|---|---|
| | | n | Mean | S.D. | n | Mean | S.D. | n | Mean | S.D. | n | Mean | S.D. | n | Mean | S.D. |
| 4 | 80/20 lac/TMC | 5 | 117 | 4.8 | 5 | 120 | 4.6 | 5 | 121 | 4.2 | 5 | 122 | 3.9 | 5 | 123 | 3.3 |
| 7 | 85/15 lac/TMC | 5 | 114 | 1.9 | 5 | 118 | 2.5 | 5 | 120 | 3.2 | 5 | 121 | 3.4 | 4 | 123 | 2.3 |
| 8 | 90/10 lac/TMC | 5 | 115 | 2.2 | 5 | 120 | 2.0 | 5 | 121 | 1.9 | 5 | 122 | 2.0 | 5 | 123 | 2.3 |
| 9 | 95/5 lac/TMC | 5 | 116 | 2.6 | 5 | 120 | 1.9 | 5 | 121 | 2.1 | 5 | 122 | 1.9 | 5 | 123 | 1.6 |

TABLE 11

Opening Strength (g)

In Vitro Time (days)

| Table 8a Sample | Polymer | Diam. (in.) | 0 Days n | 0 Days Mean | 0 Days S.D. | 7 Days n | 7 Days Mean | 7 Days S.D. | 14 Days n | 14 Days Mean | 14 Days S.D. | 21 Days n | 21 Days Mean | 21 Days S.D. | 28 Days n | 28 Days Mean | 28 Days S.D. | 35 Days n | 35 Days Mean | 35 Days S.D. | 42 Days n | 42 Days Mean | 42 Days S.D. |
|---|---|---|---|---|---|---|---|---|---|---|---|---|---|---|---|---|---|---|---|---|---|---|---|
| 1 | PLLA | 0.021 | 5 | 592 | 31.3 | 5 | 729 | 34.9 | 5 | 815 | 51.8 | 5 | 839 | 35.6 | 5 | 793 | 36.0 | 5 | 882 | 36.3 | 4 | 798 | 72.9 |
| 2 | PLLA | 0.018 | 5 | 318 | 69.8 | 5 | 454 | 80.7 | 5 | 484 | 91.3 | 5 | 598 | 65.4 | 5 | 470 | 94.1 | 5 | 520 | 47.7 | 5 | 528 | 65.9 |
| 3 | PLLA | 0.015 | 5 | 177 | 38.5 | 4 | 214 | 42.9 | 5 | 212 | 46.4 | 5 | 248 | 58.0 | 5 | 242 | 68.9 | 5 | 246 | 57.6 | 5 | 308 | 67.0 |
| 4 | 80/20 lac/TMC | 0.022 | 5 | 497 | 49.4 | 4 | 603 | 65.0 | 5 | 693 | 78.7 | 5 | 629 | 63.9 | 5 | 584 | 62.8 | 5 | 735 | 58.5 | 5 | 771 | 113.6 |
| 5 | 80/20 lac/TMC | 0.018 | 5 | 262 | 19.6 | 5 | 281 | 76.0 | 5 | 314 | 81.1 | 5 | 280 | 19.0 | 5 | 360 | 77.1 | 5 | 338 | 35.1 | 5 | 329 | 98.2 |
| 6 | 80/20 lac/TMC | 0.016 | 5 | 190 | 22.2 | 5 | 241 | 43.5 | 5 | 245 | 33.0 | 5 | 199 | 30.9 | 5 | 294 | 40.8 | 5 | 242 | 47.0 | 5 | 294 | 17.1 |
| 7 | 85/15 lac/TMC | 0.021 | 5 | 520 | 60.7 | 5 | 655 | 89.9 | 5 | 710 | 114.2 | 5 | 725 | 25.7 | 5 | 525 | 36.3 | 5 | 640 | 79.0 | 5 | 657 | 82.6 |
| 8 | 90/10 lac/TMC | 0.021 | 5 | 541 | 72.0 | 5 | 603 | 64.8 | 5 | 757 | 107.1 | 5 | 762 | 76.9 | 5 | 693 | 103.8 | 5 | 832 | 132.1 | 5 | 815 | 44.0 |
| 9 | 95/5 lac/TMC | 0.021 | 5 | 657 | 48.6 | 5 | 831 | 54.7 | 5 | 823 | 133.3 | 5 | 804 | 88.5 | 5 | 807 | 149.2 | 5 | 840 | 92.5 | 5 | 791 | 154.8 |
| 10 | 80/20 lac/cap | 0.021 | 5 | 459 | 54.8 | 5 | 706 | 90.4 | 5 | 655 | 72.2 | 5 | 755 | 40.4 | 5 | 760 | 102.3 | 5 | 751 | 72.8 | 5 | 713 | 74.2 |
| 11 | 80/20 lac/cap | 0.018 | 5 | 340 | 62.0 | 5 | 431 | 88.5 | 5 | 496 | 106.7 | 5 | 458 | 108.7 | 5 | 557 | 189.7 | 5 | 564 | 90.2 | 5 | 574 | 126.6 |
| 12 | 80/20 lac/cap | 0.015 | 5 | 205 | 118.2 | 5 | 245 | 40.8 | 5 | 410 | 163.3 | 5 | 400 | 84.0 | 5 | 214 | 20.3 | 5 | 346 | 186.3 | 5 | 221 | 99.2 |
| 13 | 95/5 lac/cap | 0.021 | 5 | 550 | 132.2 | 5 | 686 | 111.5 | 5 | 684 | 108.2 | 5 | 674 | 64.7 | 5 | 782 | 85.7 | 5 | 780 | 110.5 | 5 | 755 | 135.5 |
| 14 | 95/5 lac/cap | 0.018 | 5 | 465 | 103.4 | 5 | 660 | 121.4 | 5 | 697 | 213.3 | 5 | 716 | 186.8 | 5 | 703 | 96.6 | 5 | 718 | 308.2 | 5 | 850 | 212.9 |
| 15 | 95/5 lac/cap | 0.015 | 5 | 186 | 50.5 | 5 | 377 | 173.4 | 5 | 304 | 73.1 | 5 | 347 | 84.5 | 5 | 319 | 91.3 | 5 | 317 | 42.5 | 5 | 383 | 162.7 |
| 16 | Polyglycolide | 0.021 | 5 | 351 | 37.1 | | | | | | | | | | | | | | | | | | |
| 17 | Polyglycolide | 0.018 | 5 | 212 | 40.8 | | | | | | | | | | | | | | | | | | |
| 18 | Polyglycolide | 0.015 | 5 | 95 | 4.1 | | | | | | | | | | | | | | | | | | |
| 19 | Polyglycolide | 0.015 | 5 | 145 | 4.9 | | | | | | | | | | | | | | | | | | |
| 20 | 67/33 gly/TMC | 0.018 | 6 | 251 | 40.4 | 5 | 249* | 48.6 | 5 | 217 | 62.3 | 4 | 175 | 24.8 | 5 | 127 | 13.4 | 5 | 101 | 31.8 | 5 | 63 | 26.4 |
| 21 | 25/75 gly/lac | 0.021 | 5 | 323 | 17.4 | | | | | | | | | | | | | | | | | | |
| 22 | 25/75 gly/lac | 0.018 | 5 | 311 | 29.1 | | | | | | | | | | | | | | | | | | |
| 23 | 25/75 gly/lac | 0.015 | 5 | 117 | 25.9 | | | | | | | | | | | | | | | | | | |
| 24 | PET | 0.018 | 5 | 276 | 48.3 | | | | | | | | | | | | | | | | | | |
| 25 | PET | 0.015 | 5 | 187 | 17.5 | | | | | | | | | | | | | | | | | | |
| 26 | PET | 0.015 | 5 | 189 | 12.6 | | | | | | | | | | | | | | | | | | |
| 27 | PBT | 0.018 | | unable to form staple | | | | | | | | | | | | | | | | | | | |
| 28 | HDPE | 0.021 | 5 | 218 | 15.0 | | | | | | | | | | | | | | | | | | |
| 29 | HDPE | 0.018 | 5 | 164 | 13.0 | | | | | | | | | | | | | | | | | | |
| 30 | HDPE | 0.018 | 5 | 203 | 28.8 | | | | | | | | | | | | | | | | | | |
| 31 | HDPE | 0.018 | 5 | 157 | 25.6 | | | | | | | | | | | | | | | | | | |
| 32 | HDPE | 0.015 | 5 | 124 | 13.6 | | | | | | | | | | | | | | | | | | |
| 33 | Polybutester | 0.021 | | Unable to form staple | | | | | | | | | | | | | | | | | | | |
| 34 | Polybutester | 0.018 | | Unable to form staple | | | | | | | | | | | | | | | | | | | |
| 35 | Polybutester | 0.015 | | Unable to form staple | | | | | | | | | | | | | | | | | | | |
| 36 | PP | 0.021 | | Unable to form staple | | | | | | | | | | | | | | | | | | | |
| 37 | PP | 0.018 | | Unable to form staple | | | | | | | | | | | | | | | | | | | |
| 38 | PP | 0.015 | | Unable to form staple | | | | | | | | | | | | | | | | | | | |
| Example 13.a | 80/20 lac/TMC | 0.022 | 6 | 442 | 36.0 | 6 | 584 | 85.3 | 6 | 593 | 85.8 | | | | 6 | 621 | 57.4 | | | | | | |

TABLE 11-continued

Opening Strength (g)
In Vitro Time (days)

| Table 8a | Polymer | Diam. (in.) | 0 Days | | | 7 Days | | | 14 Days | | | 21 Days | | | 28 Days | | | 35 Days | | | 42 Days | | |
|---|---|---|---|---|---|---|---|---|---|---|---|---|---|---|---|---|---|---|---|---|---|---|---|
| | | | n | Mean | S.D. | n | Mean | S.D. | n | Mean | S.D. | n | Mean | S.D. | n | Mean | S.D. | n | Mean | S.D. | n | Mean | S.D. |
| | (EtO) | | | | | | | | | | | | | | | | | | | | | | |
| 13.b | 80/20 lac/TMC (2.5 Mrad) | 0.022 | 6 | 510 | 89.0 | 6 | 667 | 43.5 | 6 | 692 | 72.2 | | | | 6 | 734 | 162.1 | | | | | | |
| 13.c | 80/20 lac/TMC (5 Mrad) | 0.022 | 6 | 456 | 73.3 | 6 | 710 | 110.8 | 6 | 689 | 69.3 | 6 | 688 | 101.8 | 5 | 660 | 173.6 | | | | | | |
| 13.d | 80/20 lac/TMC (5 Mrad) | 0.022 | 6 | 560 | 67.4 | 6 | 543 | 76.7 | 6 | 560 | 117.7 | 6 | 641 | 96.3 | 6 | 587 | 79.2 | | | | | | |
| 13.e | 80/20 lac/cap (2.5 Mrad) | 0.021 | 5 | 524 | 44.6 | 5 | 600 | 48.6 | 5 | 627 | 56.5 | 5 | 601 | 49.9 | 5 | 523 | 101.3 | 5 | 543 | 65.6 | 5 | 514 | 55.3 |
| 13.f | 80/20 lac/cap (2.5 Mrad) | 0.018 | 5 | 283 | 48.2 | 4 | 361 | 91.2 | 5 | 356 | 66.2 | 5 | 319 | 66.6 | 5 | 345 | 92.9 | 5 | 395 | 130.0 | 4 | 340 | 70.6 |
| 13.g | 80/20 lac/cap (2.5 Mrad) | 0.015 | 5 | 153 | 13.4 | 5 | 162 | 38.2 | 5 | 192 | 27.1 | 5 | 226 | 50.9 | 5 | 202 | 16.2 | 5 | 170 | 28.7 | 5 | 197 | 31.9 |

*8 days

TABLE 12

| | Creep Test Results | | | |
|---|---|---|---|---|
| | Mean Displacement (inches) | | Percent (Displacement) | |
| Wt. in Air (grams) | 72 | 50 | 72 | 50 |
| Baseline (inches) | (0.079) | (0.074) | — | — |
| Time (days) | | | | |
| 0.042 | 0.001 | 0.001 | 1.29 | 1.38 |
| 1 | 0.006 | 0.004 | 7.62 | 5.45 |
| 3 | 0.011 | 0.009 | 13.97 | 11.79 |
| 6 | 0.014 | 0.011 | 17.74 | 14.42 |
| 8 | 0.014 | 0.011 | 17.74 | 14.42 |
| 11 | 0.014 | 0.011 | 17.74 | 14.42 |
| 13 | 0.014 | 0.011 | 17.74 | 14.42 |
| 14 | 0.014 | 0.011 | 17.74 | 14.42 |
| 17 | 0.014 | 0.011 | 17.74 | 14.42 |

What is claimed:

1. An article of manufacture comprising a one piece surgical repair device consisting essentially of a polymeric wire comprised of an oriented, semicrystalline polymer and having a Young's modulus of greater than about 600,000 psi, wherein the one piece surgical repair device is capable of permanent flexural deformation at ambient temperature.

2. The article of claim 1 wherein the polymeric wire has a diameter of about 0.005 to 0.050 inches.

3. The article of claim 2 wherein the diameter is about 0.010 to 0.025 inches.

4. The article of claim 1 wherein the Young's modulus is greater than about 800,000 psi.

5. The article of claim 4 wherein the oriented polymer is from about 20 to 70 percent crystalline.

6. The article of claim 5 wherein said oriented polymer is up to about 60 percent crystalline.

7. The article of claim 1 wherein said oriented, semicrystalline polymer is a homopolymer of polylactic acid.

8. The article of claim 1 wherein said oriented, semicrystalline polymer is a homopolymer of polyglycolic acid.

9. The article of claim 1 wherein said oriented, semicrystalline polymer is a multi-phase polymer derived from lactide and glycolide.

10. The article of claim 1 wherein said oriented, semicrystalline polymer is a block copolymer.

11. The article of claim 10 wherein the block copolymer comprises lactic acid ester linkages.

12. The article of claim 1 wherein said block copolymer comprises linkages prepared from monomers selected from the group consisting of ε-caprolactone and 1,3-dioxan-2-one.

13. The article of claim 12 wherein the lactic acid ester linkages comprise about 95 mole percent of said block copolymer.

14. The article of claim 13 wherein the remaining linkages are prepared from 1,3-dioxan-2-one.

15. The article of claim 13 wherein the remaining linkages are prepared from ε-caprolactone.

16. The article in any one of claims 2, 3, 4, or 5–15 inclusive wherein the one piece surgical repair device is a staple.

17. The article in any one of claims 2, 3 or 5–15, 6–17 inclusive wherein the one piece surgical repair device is a cerclage wire or Kirschner wire.

18. The article in any one of claims 10 to 15 wherein at least one of the continuous phases has an in vivo glass transition temperature of more than about 37° C. and comprises more than about 50 mole percent of the copolymer.

19. An article of manufacture comprising a one piece surgical staple consisting essentially of a polymeric wire comprised of an oriented, semicrystalline block copolymer having at least one continuous phase, and comprising more than about 50 mole percent of lactic acid ester linkages and the remaining linkages are prepared from ε-caprolactone, wherein the one piece surgical staple is capable of permanent flexural deformation at ambient temperature.

20. An article of manufacture comprising a one piece, sterile surgical repair device manufactured from a polymeric wire comprising an extrusile, biocompatible polymer having at least one continuous phases, at least one of the continuous phases having an in vivo glass transition temperature of more than about 37° C., wherein the one piece, sterile surgical repair device is capable of permanent flexural deformation at ambient temperature.

21. The article of claim 20 wherein the polymeric wire has a diameter of about 0.005 to 0.50 inches.

22. The article of claim 21 wherein the diameter is about 0.010 to 0.025 inches.

23. The article of claim 20, 21 or 22 wherein the polymeric wire has a Young's modulus of greater than about 600,000 psi.

24. The article of claim 23 wherein the Young's modulus is greater than about 800,000 psi.

25. The article of claim 20 wherein the extrusile, biocompatible polymer is a copolymer.

26. The article of claim 25 wherein the copolymer is a block copolymer.

28. The article of claim 25, or 26 or 27 wherein at least one of the continuous phases has an in vivo glass transition temperature of more than about 37° C. and comprises more than about 50 mole percent of the copolymer.

27. The article of claim 20 wherein the extrusile, biocompatible polymer is a multi-phase polymer derived from two different monomers.

29. The article in any one of the claims 20 to 22 or 25 to 27 wherein the one piece surgical repair device is a staple and the polymeric wire has a Young's modulus of greater than about 600,000 psi.

30. The article in any one of claims 20 to 22 or 25 to 27 wherein the one piece surgical repair device is a cerclage wire or Kirschner wire.

31. A one piece, sterile surgical staple useful in mammalian tissue, the staple comprising an extruded polymeric wire consisting essentially of an oriented, semicrystalline bioabsorbable polymer, or blend of at least two polymers wherein at least one polymer is a semicrystalline polymer, the oriented, semicrystalline bioabsorbable polymer or blend comprising a continuous phase having a glass transition temperature of greater than the in-vivo temperature of the mammalian tissue, wherein said staple is capable of permanent deformation in body fluids.

32. An article of manufacture comprising an irradiation sterilized, surgical staple manufactured from an extruded and drawn polymeric wire having a diameter of about 0.005 to 0.050 inches, the polymeric wire comprising a bioabsorbable polymer having at least one continuous phases, the at least one continuous phase having an in vivo glass transition temperature of more than about 37° C., wherein the irradiation sterilized, surgical staple is capable of permanent flexural deformation, has a Young's modulus of greater than about 800,000 psi, and maintains at least about 50 percent of its initial opening strength after 21 days in vivo.

33. The article of claim 32 wherein said irradiation sterilized, surgical staple is one piece.

34. The article of claim 33 wherein the bioabsorbable polymer is a homopolymer of polylactic acid.

35. The article of claim 32 wherein the extruded and drawn polymeric wire has a diameter of about 0.010 to 0.025 inches.

36. The article of claim 33 wherein the bioabsorbable polymer is a homopolymer of polyglycolic acid.

37. The article of claim 32 wherein the bioabsorbable polymer is a copolymer.

38. The article of claim 37 wherein the copolymer comprises more than about 50 mole percent of glycolic acid ester linkages.

39. The article of claim 38 wherein said irradiation sterilized, surgical staple maintains about 100 percent after 7 days and greater than about 70 percent after 21 days in vivo of its initial opening strength.

40. The article of claim 37 wherein the copolymer comprises lactic acid ester linkages.

41. The article of claim 40 wherein the block copolymer comprises linkages prepared from monomers selected from the group consisting of ε-caprolactone and 1,3-dioxan-2-one.

42. The article of claim 40 wherein the copolymer is a block copolymer and comprises more than about 50 mole percent of lactic acid ester linkages.

43. The article of claim 42 wherein the remaining linkages are prepared from 1,3-dioxan-2-one.

44. An article of manufacture comprising an irradiation sterilized, surgical staple consisting essentially of an extruded and drawn polymeric wire having a diameter of about 0.005 to 0.050 inches, the polymeric wire comprising a bioabsorbable block copolymer having at least about 80 mole percent of lactic acid ester linkages and the remaining linkages are prepared from ε-caprolactone, and comprising at least one continuous phases, the at least one continuous phase having an in vivo glass transition temperature of more than about 37° C., wherein the irradiation sterilized, surgical staple is capable of permanent flexural deformation, has a Young's modulus of greater than about 800,000 psi, and maintains at least about 50 percent of its initial opening strength after 21 days in vivo.

45. The article of claim 43 or 44 wherein the lactic acid ester linkages comprise about 95 mole percent of the block copolymer.

46. The article as in any one of claims 40 to 44 wherein said irradiation sterilized, surgical staple maintains greater than about 110 percent of its initial opening strength from about 7 to 21 days in vivo.

* * * * *